United States Patent
Gada et al.

(10) Patent No.: US 10,022,906 B2
(45) Date of Patent: Jul. 17, 2018

(54) METHODS FOR SOLID PHASE PROCESSING OF TUBES AND MEDICAL DEVICES MADE FROM THE PROCESSED TUBES

(71) Applicant: Abbott Cardiovascular Systems Inc., Santa Clara, CA (US)

(72) Inventors: Manish B. Gada, Santa Clara, CA (US); Bobby B. Speed, Murrieta, CA (US); James P. Oberhauser, Saratoga, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 331 days.

(21) Appl. No.: 14/810,344

(22) Filed: Jul. 27, 2015

(65) Prior Publication Data

US 2016/0031150 A1  Feb. 4, 2016

Related U.S. Application Data

(60) Provisional application No. 62/031,115, filed on Jul. 30, 2014.

(51) Int. Cl.
 *B29C 55/26* (2006.01)
 *B29C 65/56* (2006.01)
 (Continued)

(52) U.S. Cl.
 CPC .............. *B29C 55/26* (2013.01); *A61F 2/82* (2013.01); *A61L 31/06* (2013.01); *A61L 31/148* (2013.01);
 (Continued)

(58) Field of Classification Search
 CPC ........ A61F 2/01; A61F 2002/018; A61F 2/82; A61F 2/844; A61F 2/91–2/91591; A61F 2210/0004; A61F 2240/00–2240/001; A61F 2250/0028; B29C 49/00; B29C 49/0015; B29C 49/08; B29C 55/30; B29C 49/02; B29C 49/10; B29C 55/24;
 (Continued)

(56) References Cited

U.S. PATENT DOCUMENTS

| 4,801,419 A * | 1/1989 | Ward | B29C 55/30 264/288.4 |
|---|---|---|---|
| 7,687,002 B2 * | 3/2010 | Nichols | B29C 55/30 264/164 |

(Continued)

FOREIGN PATENT DOCUMENTS

| EP | 0 157 601 | 5/1991 |
|---|---|---|
| WO | WO 2014/045068 | 3/2014 |

OTHER PUBLICATIONS

Coates et al., "Drawing of polymers through a conical die", Polymer vol. 20, pp. 1553-1560, Dec. 1979.

(Continued)

*Primary Examiner* — Matthew P Travers
(74) *Attorney, Agent, or Firm* — Squire Patton Boggs (US) LLP

(57) ABSTRACT

A polymer tube is processed using a solid phase process for improving mechanical characteristics of the tube, including radial strength and stiffness. The tube is made into a scaffold possessing improved mechanical and use characteristics, such as a reduced crimped profile and improved deliverability.

17 Claims, 17 Drawing Sheets

(51) Int. Cl.
*A61F 2/82* (2013.01)
*B29C 49/00* (2006.01)
*B29C 49/64* (2006.01)
*B23P 11/00* (2006.01)
*B29C 49/08* (2006.01)
*B29K 67/00* (2006.01)
*B29L 31/00* (2006.01)
*A61L 31/06* (2006.01)
*A61L 31/14* (2006.01)
*B29L 23/00* (2006.01)

(52) U.S. Cl.
CPC .......... *B29C 49/0015* (2013.01); *B29C 49/64* (2013.01); *B29C 65/565* (2013.01); *A61F 2210/0004* (2013.01); *A61F 2240/001* (2013.01); *B23P 11/005* (2013.01); *B29C 49/08* (2013.01); *B29K 2067/046* (2013.01); *B29K 2995/006* (2013.01); *B29K 2995/0077* (2013.01); *B29K 2995/0082* (2013.01); *B29L 2023/00* (2013.01); *B29L 2031/7532* (2013.01)

(58) Field of Classification Search
CPC ..... B29C 55/26; B29D 23/00; B29L 2023/00; B29L 2031/7532; B29L 2031/7534
USPC .......................................................... 264/534
See application file for complete search history.

(56) References Cited

U.S. PATENT DOCUMENTS

| | | |
|---|---|---|
| 2007/0207186 A1 | 9/2007 | Scanlon et al. |
| 2011/0049751 A1 | 3/2011 | Gada et al. |
| 2011/0062638 A1 | 3/2011 | Glauser et al. |
| 2011/0066222 A1 | 3/2011 | Wang et al. |
| 2011/0190871 A1 | 8/2011 | Trollsas et al. |
| 2012/0042501 A1 | 2/2012 | Wang et al. |
| 2013/0255853 A1 | 10/2013 | Wang et al. |
| 2014/0114399 A1 | 4/2014 | Hossainy et al. |
| 2014/0228929 A1* | 8/2014 | Huang ................ B29C 47/0023 623/1.11 |
| 2015/0230946 A1* | 8/2015 | Al-Lamee ................ A61F 2/82 623/1.15 |

OTHER PUBLICATIONS

Coates et al., "Die drawing for shape memory polymers for soft tissue fixation", Proceedings of the Polymer Processing Soc. 29 th Annual Meeting, Jul. 15-23, 2013 Nuremberg DE, Abstract 1 pg.
Notification of Transmittal of the International Search Report and the Written Opinion of the International Searching Authority, or the Declaration for PCT/US2015/042673 dated Dec. 21, 2015, 23 pages.

* cited by examiner

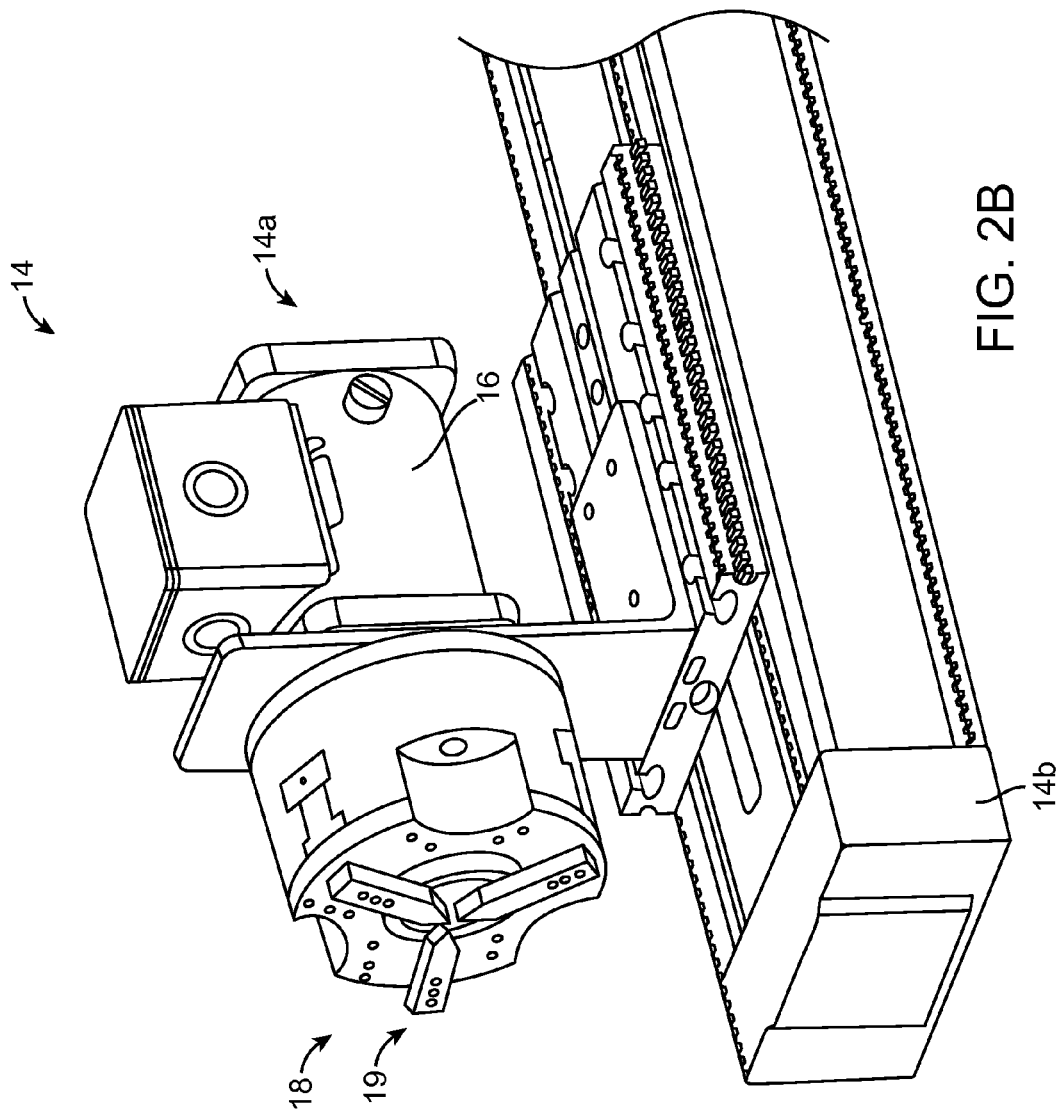

FIG. 4A

PROCESS 1

| Outgoing Tube Dimensions | | | Draw Ratios | | | Incoming Tube Dimensions | | |
|---|---|---|---|---|---|---|---|---|
| OD (in) | ID (in) | Wall (in) | Ro | Ri | Axial | OD (in) | ID (in) | Wall (in) |
| 0.1365 | 0.1285 | 0.0040 | 4.0 | 4.0 | 10% to 50% | 0.5460 | 0.5140 | 0.0160 |
| 0.1365 | 0.1295 | 0.0035 | 4.0 | 4.0 | 10% to 50% | 0.5460 | 0.5180 | 0.0140 |
| 0.1365 | 0.1285 | 0.0040 | 3.0 | 3.0 | 10% to 50% | 0.4095 | 0.3855 | 0.0120 |
| 0.1365 | 0.1295 | 0.0035 | 3.0 | 3.0 | 10% to 50% | 0.4095 | 0.3885 | 0.0105 |
| 0.1365 | 0.1285 | 0.0040 | 2.0 | 2.0 | 10% to 50% | 0.2730 | 0.2570 | 0.0080 |
| 0.1365 | 0.1295 | 0.0035 | 2.0 | 2.0 | 10% to 50% | 0.2730 | 0.2590 | 0.0070 |

FIG. 4B

PROCESS 2

| Outgoing Tube Dimensions | | | Draw Ratios | | | Incoming Tube Dimensions | | |
|---|---|---|---|---|---|---|---|---|
| OD (in) | ID (in) | Wall (in) | Ro | Ri | Axial | OD (in) | ID (in) | Wall (in) |
| 0.1365 | 0.1285 | 0.0040 | 1.5 | 1.5 | 10% to 50% | 0.2048 | 0.1928 | 0.0060 |
| 0.1365 | 0.1295 | 0.0035 | 1.4 | 1.4 | 10% to 50% | 0.1911 | 0.1813 | 0.0049 |
| 0.1365 | 0.1295 | 0.0035 | 1.3 | 1.3 | 10% to 50% | 0.1706 | 0.1684 | 0.0011 |
| 0.1365 | 0.1295 | 0.0035 | 1.2 | 1.2 | 10% to 50% | 0.1638 | 0.1554 | 0.0042 |
| 0.1365 | 0.1295 | 0.0035 | 1.1 | 1.1 | 10% to 50% | 0.1502 | 0.1425 | 0.0039 |

PROCESS 3

| Outgoing Tube Dimensions | | | Draw Ratios | | | Incoming Tube Dimensions | | |
|---|---|---|---|---|---|---|---|---|
| OD (in) | ID (in) | Wall (in) | Ro | Ri | Axial | OD (in) | ID (in) | Wall (in) |
| 0.1365 | 0.1285 | 0.0040 | 1.5 | 1.5 | 10% to 50% | 0.2048 | 0.1928 | 0.0060 |
| 0.1365 | 0.1295 | 0.0035 | 1.4 | 1.4 | 10% to 50% | 0.1911 | 0.1813 | 0.0049 |
| 0.1365 | 0.1295 | 0.0035 | 1.3 | 1.3 | 10% to 50% | 0.1706 | 0.1684 | 0.0011 |
| 0.1365 | 0.1295 | 0.0035 | 1.2 | 1.2 | 10% to 50% | 0.1638 | 0.1554 | 0.0042 |
| 0.1365 | 0.1295 | 0.0035 | 1.2 | 1.1 | 10% to 50% | 0.1570 | 0.1425 | 0.0073 |
| 0.1365 | 0.1295 | 0.0035 | 1.1 | 1.1 | 10% to 50% | 0.1502 | 0.1425 | 0.0039 |

FIG. 4C

PROCESS 4

| Outgoing Tube Dimensions | | | Draw Ratios | | | Incoming Tube Dimensions | | |
|---|---|---|---|---|---|---|---|---|
| OD (in) | ID (in) | Wall (in) | Ro | Ri | Axial | OD (in) | ID (in) | Wall (in) |
| 0.1365 | 0.1285 | 0.0040 | 1.5 | 1.5 | 10% to 50% | 0.2048 | 0.1928 | 0.0060 |
| 0.1365 | 0.1295 | 0.0035 | 1.4 | 1.4 | 10% to 50% | 0.1911 | 0.1813 | 0.0049 |
| 0.1365 | 0.1295 | 0.0035 | 1.3 | 1.3 | 10% to 50% | 0.1706 | 0.1684 | 0.0011 |
| 0.1365 | 0.1295 | 0.0035 | 1.2 | 1.2 | 10% to 50% | 0.1638 | 0.1554 | 0.0042 |
| 0.1365 | 0.1295 | 0.0035 | 1.1 | 1.1 | 10% to 50% | 0.1502 | 0.1425 | 0.0039 |
| 0.1365 | 0.1285 | 0.0040 | 1.5 | 1.5 | 10% to 50% | 0.2048 | 0.1928 | 0.0060 |

FIG. 4D

PROCESS 5

| Outgoing Tube Dimensions | | | Draw Ratios | | | Incoming Tube Dimensions | | |
|---|---|---|---|---|---|---|---|---|
| OD (in) | ID (in) | Wall (in) | Ro | Ri | Axial (%) | OD (in) | ID (in) | Wall (in) |
| 0.1365 | 0.1285 | 0.0040 | 5.0 | 5.0 | 25 | 0.0581 | 0.0214 | 0.0200 |
| 0.1365 | 0.1295 | 0.0035 | 1.4 | 5.0 | 25 | 0.0683 | 0.0216 | 0.0233 |
| 0.1365 | 0.1295 | 0.0035 | 1.3 | 4.0 | 25 | 0.0910 | 0.0259 | 0.0326 |
| 0.1365 | 0.1295 | 0.0035 | 1.2 | 3.0 | 25 | 0.0341 | 0.0324 | 0.0009 |
| 0.1365 | 0.1295 | 0.0035 | 1.2 | 2.0 | 25 | 0.0683 | 0.0432 | 0.0125 |
| 0.1365 | 0.1295 | 0.0035 | 1.1 | 1.1 | 25 | 0.0683 | 0.0216 | 0.0233 |

FIG. 4E

METHODS FOR SOLID PHASE PROCESSING OF TUBES AND MEDICAL DEVICES MADE FROM THE PROCESSED TUBES

RELATED APPLICATIONS

This application claims the benefit of U.S. Provisional Application No. 62/031,115 filed Jul. 30, 2014, the entire contents of which are hereby incorporated by reference.

BACKGROUND OF THE INVENTION

Field of the Invention

The present invention relates to bioresorbable scaffolds; more particularly, this invention relates to bioresorbable scaffolds for treating vessels of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or placed on a balloon. Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent must be capable of radial compressive forces imposed on the stent as it supports the walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

The present application adopts the definitions of radial strength and radial stiffness set forth in US2014/0114399. Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. A radial "stiffness" refers to the amount net radial inward force (i.e., uniform radial inward pressure over the entire abluminal scaffold surface×the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, for example, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is for a limited duration. However, there are numerous challenges to overcome when developing a polymeric scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymer such as PLLA or PLGA.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, with motions in different directions, especially when located close to an articulating joint. As such, a scaffold intended for a peripheral vessel will need to be able to sustain more complex loading, including a combination of axial, bending, torsional and radial loading. These and related challenges facing peripherally implanted scaffolds are discussed in US2011/0190871 and US2014/0114399.

Strain hardening of tubes is known. Examples of processes for strain-hardening tubes include US20110066222; Coates, P. D. et al., *Drawing of polymers through a conical die*, POLYMER, Vol. 20, December (1979), and Coates, P. D. et al., *Die drawing for shape memory polymers for soft tissue fixation*, Proceedings of the Polymer Processing Society 29th Annual Meeting, Jul. 15-23, 2013, Nuremberg Germany.

A continued need exists for improving the mechanical properties of scaffolds, for both coronary and peripheral applications.

SUMMARY OF THE INVENTION

A process for improving the mechanical properties of polymer tubes according to the invention includes combinations of blow-molding and solid phase processing of the tube material, or solid phase processing without blow molding. According one aspect of invention there is a medical device made from a tube processed in one of the foregoing manners. In some embodiments the medical device is a scaffold produced by one of these processes. The scaffold can have one or more of a smaller strut width and/or link width and/or wall thickness as a known scaffold made from the same or similar starting material, yet due to the manner in which the starting material is processed a scaffold according to the invention can have the same or similar strength and stiffness properties, such as a similar flexural rigidity, EI (the product E×I where E is the Young's modulus of the processed material and I is the cross-sectional moment of inertia of a strut/link about the axis of bending) as the known scaffold having the larger link and/or strut width and/or larger wall thickness.

According one aspect the processed scaffold is capable of achieving a smaller crimp profile, greater expansion capability, or higher ratio of crimp to pre-crimp diameter, and/or fully maximum expansion (before cracking) to fully crimped diameter. Additionally, or separately, the scaffold can have improved deliverability, e.g., increased longitudinal flexibility, while possessing the same or similar toughness, radial strength and/or radial stiffness properties of a scaffold.

In some embodiments the tube is made from an extruded, high molecular weight polymer or polymer combination. The tube may be an amorphous or substantially amorphous tube. The extruded tube is bi-axially expanded by blow-molding. The blow-molded tube is then subject to a solid-phase process characterized by further radial deformation of the tube at temperatures close to, and above the Tg of the polymer composition. "Close to" in this respect means from about 5-10Deg. C., 5-20Deg. C. or up to about 30Deg. C. above Tg of the polymer composition of the extruded tube. The solid-phase process is characterized by die drawing whereby there is a further radial or circumferential deformation of the blow-molded tube, which results in further alignment of polymer chains along strain direction(s). The resultant strain-hardened tube has improved mechanical properties over the blow-molded tube.

In other embodiments a polymer tube is not first blow-molded. Instead, an extruded tube, preferably but not necessarily an amorphous tube, is subject to the die drawing process without any substantial prior radial or axial deformation of the extruded tube.

It is believed that by practice of one or more of the strain hardening processes in accordance with the invention the processed polymer tube, i.e., a tube subjected to a blow-molding process followed by a solid phase process, or subjected to only the solid phase process (no blow molding)

according to the invention, has increased anisotropic properties over the thickness of the tube. There can be increased circumferential alignment of polymer chains resulting from both the blow molding and sold phase process, or only the solid phase process resulting in increased strength and stiffness properties.

An extruded tube has been radially strengthened/stiffened by only the blow-molding process, e.g., the blow molding process described in US20110066222. Using this process an extruded tube may be radially expanded by about 400% from its original diameter. The resulting radially expanded tube exhibits certain non-uniformities in polymer chain alignment over the radially expanded tube's wall thickness. During a radial or biaxial blow-molding expansion process non-uniformities in polymer chain alignment are believed to be caused by one or both of thermal non-uniformities and strain non-uniformities present during the blow-molding.

Radial expansion by internal pressurization within a tubular mold produces a strain gradient over the wall thickness. The degrees of strain in the radial direction, or hoop strain increases from the outside surface of the tube to the inside surface. That is, the percentage strain for areas close to the inner diameter of the tube, compared with the outer diameter of the tube, will be higher for the same draw ratios of inner and outer diameters. As a consequence, the amount of radial strain near the outer surface (for a given set of processing conditions, e.g., processing temperature) of the tube can be limited by the level of strain that can be withstood before cracks, voids or fractures begin to form near the inner surface. Thus, strain non-uniformity across the wall thickness may be considered an inherent byproduct of blow molding processes.

Thermal non-uniformity refers to a temperature gradient arising from various mechanisms of heat transfer during blow-molding, e.g., radiation, conduction, and convection. Circumferentially orientated polymer chains that are close to a heat source may revert back to their original state shortly after radial expansion. For example, for a tube heated by an external heat source the outer surface of the tube will experience higher and/or more prolonged exposure to elevated temperatures than the inner surface of the tube. While the expanded tube is maintained at temperatures above Tg there is greater mobility among the polymer chains, which can cause a reversion back to a more isotropic or random state of alignment. Hence, the polymer chains closer to the outer surface can have a tendency to revert back to their pre-strained orientation.

According to another aspect there is a process for improving mechanical properties in a polymer tube including avoiding strain non-uniformity or improving anisotropic properties of the tube over the wall thickness. A process according to some embodiments subjects a tube to a blow molding process followed by a solid phase process where the combined processes increase the anisotropy across the tube thickness. A greater degree of uniformity, or less non-uniformity in polymer chain alignment across the wall thickness is achieved. When polymer chains close to the inner and outer surfaces are circumferentially aligned, as opposed to predominantly only the inner surface, radial strength and stiffness properties of the tube and scaffold made from the tube are improved.

Additional aspects include a scaffold comprising a body formed of longitudinally-spaced rings interconnected by links, the rings including a plurality of struts connected at crowns, wherein the body includes rings having 6 crowns connected by 3 links to adjacent rings, wherein the struts have a wall thickness of 90-110 microns, wherein the scaffold is made of a blend of a poly(L-lactide) (PLLA) with a PLLA and polycaprolactone (PCL) random copolymer, and wherein the caprolactone units are 1 to 5 wt % of the blend.

The scaffold may include one or more or any combination of the following aspects: wherein a crystallinity of the blend is 20 to 50%; wherein a crystallinity of the blend is 40 to 50%; wherein the links connect the rings at a W-crown of one ring and Y-crown of an adjacent ring; wherein the struts have a width of 120 to 150 microns; wherein the scaffold is formed from a strain hardened tube having differently oriented inner and outer layers of polymer chains, where the outer layer has polymer chains arranged substantially in a first direction and the inner layer has polymer chains oriented substantially in a second direction, wherein the one of the first or second directions have a higher axial orientation component than the other of the first and second directions by an amount equal to about 10-100%; wherein the struts and links form a plurality of symmetric cells; wherein the struts and links form a plurality of asymmetric cells; and wherein the scaffold is made completely of the blend.

According to another aspect of invention there is a solid phase process performed on an incoming tube (either an amorphous tube or radially expanded tube). The process produces a greater degree of, or less non-uniformity in polymer chain alignment across the wall thickness than a tube processed by only blow-molding.

According to some embodiments a solid phase process is performed briefly, meaning the tube is subjected to the elevated temperatures for only a brief period of time, e.g., about 10 seconds only at a temperature close to, and above the glass transition temperature (Tg). In contrast, a known blow-molding such as described in US 2011/0066222 subjects the expanded material to temperatures above Tg for about up to 30 or 40 seconds where more than half of this time period corresponds to the having the elevated temperature after the tube portion has been biaxially expanded.

According to some embodiments the process further includes a quenching step to rapidly reduce the temperature of the tube when it exits a die. This may be desired to help maintain or lock-in a polymer chain alignment or desired anisotropic properties of the strain-hardened material across the wall thickness.

According to some embodiments a solid phase process produces higher draw ratios for the tube outer diameter than the inner diameter, with the result that about the same level of strain exists near the inner surface and outer surface of the tube. One advantage of this differential draw ratio between inner and outer diameter is that a lower processing temperature can be used, in addition to producing more uniformity in strain across the wall thickness.

Tubes processed according to the invention permit scaffolds to be made having patterns that allow reduced crimping profiles and/or greater expansion ranges due to the improved mechanical properties of the tube form which the scaffold is made. With respect to crimp profile, it is contemplated that a scaffold strut cross-sectional area (width× thickness) can be decreased by as much as ½ of current cross-sectional area dimensions for the same polymer material. For example, in the case of a scaffold made from PLLA, for tubes processed according to the invention it is believed that a same or similar radial strength, radial stiffness and fracture toughness properties as the Abbott Vascular ABSORB™ scaffold product can be made for a scaffold with a wall thickness of 100 microns or less than 100 microns (the ABSORB™ scaffold has a wall thickness of 152 microns). Alternatively, or in addition a strut width may be from about 100 to 150 microns, as compared to the ABSORB™ without losing radial strength or stiffness properties.

According to additional aspects of invention, there is a strain hardened tube, a process for making a strain-hardened tube, a system for solid phase processing, a solid phase process, and a combination blow-molding and solid phase process for making a tube that is later made into a scaffold, a medical device or scaffold, a method for making such a scaffold from the tube, or method for assembly of a medical device comprising such a scaffold having one or more, or any combination of the following aspects of the disclosure (1)-(24):

(1) A method for making a medical device, comprising: forming a tube comprising a polymer or a polymer combination; radially expanding the tube; die drawing the radially expanded tube; and making a scaffold from the die drawn tube.

(2) A scaffold having a pattern according to FIGS. 6-7 or Table 2.

(3) A strut of a scaffold formed from a tube according to any of Processes 1-6, the tube being made from a polymer composition, wherein the strut has a flexural rigidity that is about equal to the flexural rigidity of a scaffold (4) A tube made from a high molecular weight polymer, e.g., a number average molecular weight (Mn) of a PLA-PCL combination is 200 to 500 kDa or 300 to 500 kDa.

(5) A die with or without a mandrel, configured for imposing a strain gradient on a tube, wherein the strain increases from an inner to outer surface of the tube or from the outer to inner surface.

(6) A method for increasing a strain nearer to an outer surface of a tube, or increasing a strain nearer to an inner surface than an outer surface of the tube including die drawing the tube through a draw down or draw up die.

(7) Increasing a strain gradient such that an inner surface has a higher strain than an outer surface comprising die drawing a tube through a die having a tapered mandrel.

(8) Increasing a strain gradient such that an outer surface has a higher strain than an inner surface comprising die drawing a tube through a die having a cylindrical mandrel or no mandrel and a draw down die.

(9) A feed in tube for a die comprising an amorphous tube or a blow-molded tube.

(10) A method of making a strain hardened tube having differently oriented inner and outer layers of polymer chains ("inner layer of polymer chains" means orientated polymer chains located closer to an inner surface of the tube than an outer surface and "outer layer of polymer chains" means orientated polymer chains located closer to an outer surface of the tube than the inner surface), comprising a first radial expansion and/or contraction of a tube to produce a tube having a radial draw of R1, followed by a second radial expansion and/or contraction of a tube to produce a tube having a radial draw of R2, wherein the axial draw associated with R1 is substantially greater than the axial draw associated with R2.

(11) The first or second radial expansion/contraction has an axial draw that is about 5, 10, 15, 20, 50 and 50-100 times greater than an axial draw for the other of the first and second radial expansion/contraction; and R1=R2, R1>R2 or R2<R1.

(12) A strain hardened tube or scaffold having differently oriented inner and outer layers of polymer chains, where the outer layer has polymer chains arranged substantially in a first direction and the inner layer has polymer chains oriented substantially in a second direction, wherein the one of the first or second directions have a higher axial orientation component than the other of the first and second directions by an amount equal to 10% to 100%.

(13) A method of making a scaffold from a tube including any one of, or any combination of the following things
(a) through ( ):
    (a) the tube is made from a high molecular weight polymer, e.g., a number average molecular weight (Mn) of a PLA-PCL combination is 200 to 500 kDa or 300 to 500 kDa;
    (b) the tube is substantially or completely a blend of polylactide (PLA) and a PLA and polycaprolactone (PCL) random copolymer (20% PCL) and the blended PLA-PCL combination has between about 1% to 5% by weight PCL;
    (c) the tube is made from an extruded polymer having a crystallinity of less than 10% or this extruded tube is an amorphous tube;
    (d) the tube is radially expanded by blow molding, wherein the ratio of RE/AE is between about 1.05 to 1.0, 2 to 1, 2.5 to 1, 3 to 1, and 4 to 1;
    (e) the tube is subject to die drawing including pulling the tube through a die that reduces or increases the diameter of the tube;
    (f) the tube is subject to die drawing including pulling the tube through a die that is devoid of a mandrel;
    (g) the tube is subject to die drawing including pulling the tube through a die that includes a flat or tapered mandrel;
    (h) an inner draw ratio of the drawn tube is lower than an outer diameter draw ratio of the deformed tube;
    (i) the inner draw ratio is equal to, less than or greater than the outer draw ratio when the tube is die drawn; and/or
    (j) the die for die drawing the tube has a temperature of about 10 to 20, 5-20 or 20-30 degrees Celcius above the glass transition temperature (Tg) of the tube material.

(14) A method for making a medical device, further including: crimping the scaffold to a balloon, the balloon having an inflated diameter and the scaffold having a pre-crimp diameter before crimping and crimped diameter after crimping, wherein the scaffold undergoes a significant plastic deformation when crimped to the balloon, and wherein the scaffold crimped diameter is at least 2 times less than the pre-crimp diameter and/or the balloon inflated diameter; wherein the scaffold a first and second ring with between 7 to 12 crowns and at most 2, or at most 3 links connecting the first and second rings; and/or wherein the scaffold forms a plurality of symmetric cells or asymmetric cells; wherein the scaffold forms patterns of rings interconnected by links, wherein the number of links and crowns include any of those listed in Table 2.

(15) A method for making a scaffold, comprising: providing a tube comprising a polymer or polymer combination; die drawing the tube; and forming the scaffold from the die drawn tube.

(16) A method of making a medical device such as a scaffold from a tube including improving stress and strain properties of the tube by die drawing, wherein the processing parameters for die drawing include any of, any combination of or all of (a)-(h):

(a) a Die Temperature (Td) between about 10 and 35° C. above Tg of the tube material;

(b) a Steady State Draw Speed (Vd) of between 0.1 mm/sec and 25 mm sec;

(c) a Die Taper angle and/or mandrel (θ) between 15 and 60 degrees;

(d) a Pre-Heat Temperature (Tp) about 5-10 degrees Celcius below a Tg of the tube material;

(e) a Temperature difference between a pre-heat chamber and a die (Delta-Tin) about 10 to 40° C.;

(f) a Quench Temperature (Tq) about 15Deg. C. or temperature causing a tube temperature to drop below 5-10Deg. C. less than Tg within 1-2 sec from when the tube exits the die;

(g) a forced airflow into a cooling chamber (between about 5-10Deg. C.) cools exit tube material to about 15° C. within 25 mm from exit of die, the forced air is between about 5 to 10° C., or a chamber exposes the outgoing tube to ambient air for cooling; and (h) Temperature difference between die and chamber 30 (Delta-Tout) about 50 to 80° C.;

(17) wherein the method of (16) further includes one or more, or any combination of (a) through (h)

(a) an incoming tube diameter is between about 0.6 and 0.2 inches and an incoming tube thickness is about 0.02 and 0.01 inches;

(b) wherein the tube is formed by extrusion of a copolymer resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g;

(c) wherein the die drawn tube has an outer diameter draw ratio (Ro) and an inner diameter draw ratio (Ri) and Ro is greater than, less than, or about equal to Ri;

(d) wherein the tube is made from a polymer combination including PLA, and the PLA polymer of the combination may include poly(L-lactide) (PLLA), poly(D,L-lactide) having a constitutional unit weight-to-weight (wt/wt) ratio of about 96/4, poly(lactide-co-glycolide), poly(L-lactide-co-glycolide), poly(D,L-lactide-co-glycolide), poly(D,L-lactide) made from meso-lactide, and poly(D,L-lactide) made from polymerization of a racemic mixture of L- and D-lactides, and/or PLA polymer includes poly(D,L-lactide) having a constitutional unit weight-to-weight (wt/wt) ratio of about 93/7, about 94/6, about 95/5, about 96/4, about 97/3, about 98/2, or about 99/1;

(e) the incoming tube may include a PLA and PCL random copolymer. The tube may be made substantially or completely of the copolymer. The copolymer may include poly(L-lactide-co-caprolactone), poly(D,L-lactide-co-caprolactone), poly(L-lactide-co-glycolide-co-caprolactone), and poly(DL-lactide-co-glycolide-co-caprolactone);

(f) wherein the crystallinity of the drawn tube is 20 to 50%, 20 to 25%, 25 to 30%, 30 to 35%, 35 to 40%, 40 to 45%, or 45 to 50%;

(g) wherein the tube is a blend of a PLA polymer with a PCL homopolymer, including PLLA, poly(L-lactide-co-glycolide), poly(D,L-lactide-co-glycolide), and poly(D,L-lactide), wherein PLA polymers with D,L-lactide are made from a racemic mixture of L- and D-lactide or may include 1 to 15% of D constitutional units; and/or (h) wherein the drawn tube has any of the combinations of the inner and outer diameter draw ratios of FIGS. 4A, 4B, 4C, 4D and 4E.

(18) A crush-recoverable scaffold comprising a ratio of pre-crimp or tube (from which scaffold was cut) diameter to wall thickness of between 30 and 60, or between 20 and 45, the scaffold exhibiting an over 80% or over 90% recovery of a pre-crush diameter after a 0, 1 or 5 minute duration crush of magnitude 50%, 35%, or 25% of the pre-crush diameter, e.g., expanded, inflated or pre-crimp diameter. As an example, the scaffold has a 5 mm diameter before it is crimped to a balloon (i.e., a pre-crimp diameter) and is crushed by an amount equal to 35% of this diameter (1.75 mm) and held in this crushed state for 0, 1 or 5 minutes before the crush load is removed. The scaffold then returns to over 80% (4.0 mm) or over 90% (4.5 mm) of the pre-crimp diameter.

(19) A method for making a scaffold, comprising: providing a tube comprising a polymer or polymer combination; die drawing the tube; and forming the scaffold from the die drawn tube, including: forming a first and a second ring, each of which including a plurality of interconnected struts forming crowns, links connecting the first ring to the second ring, and wherein the scaffold has an outer diameter of about 3.0 mm and a wall thickness of between 80 and 100 microns, or an outer diameter of between 7-9 mm and a wall thickness of 150 to 190 microns.

(20) A first scaffold having a strut wall thickness of 80-89, 90-100, or 100-110 microns, and/or a strut width of 100-120 or 120-150 microns; wherein the flexural rigidity of the strut of the first scaffold is about equal to the flexural rigidity of a second strut made from a blow-molded tube made into a second scaffold as described in 2011/0066222 and having a thickness of greater than 150 microns and width greater than 150 microns, wherein the scaffold pattern and blow-molding process is identical between the first and second scaffolds, but the first scaffold is additionally die drawn according to the invention before being cut into the identical scaffold pattern as the second scaffold.

(21) A medical device, comprising: a strain hardened tube or a scaffold made from the tube having differently oriented inner and outer layers of polymer chains; wherein the outer layer has polymer chains arranged substantially in a first direction and the inner layer has polymer chains oriented substantially in a second direction; and wherein one of the first or second directions have a higher axial orientation component than the other of the first and second directions by an amount equal to about 10-100%.

(22) A scaffold, comprising: a strut wall thickness of 80-89, 90-100, or 100-110 microns, and/or a strut width of 100-120 or 120-150 microns; and the scaffold being laser cut from a tube of a polymer composition; wherein the flexural rigidity of the strut is about equal to the flexural rigidity of a strut made from a blow-molded tube made into the same scaffold as described in 2011/0066222 and having a thickness of greater than 150 microns, width greater than 150 microns and using the same extruded tube material.

(23) The scaffold of (22), wherein the scaffold has polymer chains located closer an outer surface than inner surface of the tube orientated substantially in the radial direction, wherein polymer chains closer to the outer than inner surface for the scaffold described in US Pub. 2011/0066222 have substantially no radial orientation.

(24) The scaffold of (22) or (23), wherein the axial component of orientated polymer chains closer to the outer surface of the tube are less than, greater than, or equal to the axial component of orientated polymer chains closer to the inner surface.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 2B is a perspective view of the second portion of the apparatus for die drawing a tube. The second portion includes a gripper and a sled for drawing the tube through the die of the first portion at a draw speed Vd.

FIG. 4A is a table showing an incoming and final tube dimensions, and inner and outer draw ratios for an incoming tube processed using the die of FIG. 3A.

FIG. 4B is a table showing an incoming and final tube dimensions, and inner and outer draw ratios for an incoming tube processed using the die of FIG. 3A.

FIG. 4C is a table showing an incoming and final tube dimensions, and inner and outer draw ratios for an incoming tube processed using the die of FIG. 3B.

FIG. 4D is a table showing an incoming and final tube dimensions, and inner and outer draw ratios for an incoming tube processed using the die of FIG. 3C.

FIG. 4E is a table showing an incoming and final tube dimensions, and inner and outer draw ratios for an incoming tube processed using the die of FIG. 3E.

DETAILED DESCRIPTION

Figure 1:
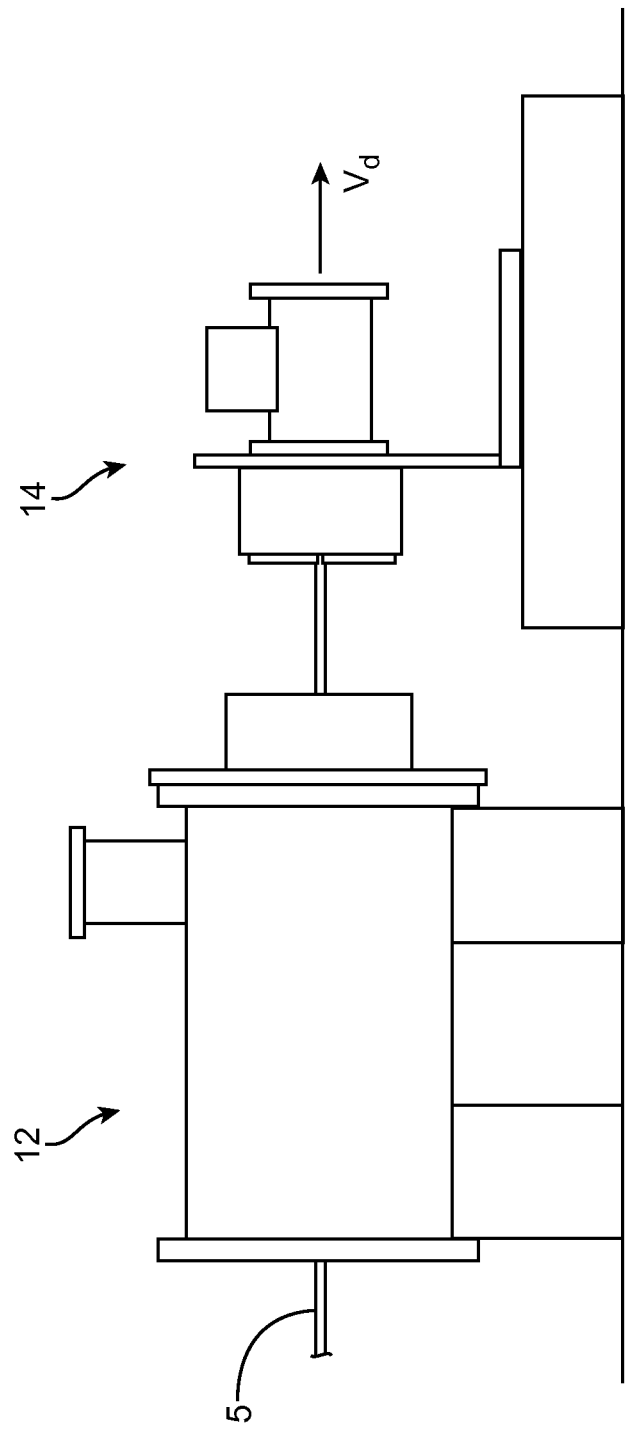
FIG. 1 is a side view of an apparatus for die drawing a tube. The apparatus has a first portion and a second portion.

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

"Amorphous" or "substantially amorphous" means no greater than, or less than 5% crystallinity, or not more than 1%, 2% or 4% crystallinity.

The "degree of crystallinity" may be expressed in terms of, $w_c$ (mass fraction), $\varphi_c$ (volume fraction) and refers to mass fraction or volume fraction of crystalline phase in a sample of polymer. The mass-fraction and the volume-fraction degrees of crystallinity are related by the equation, $w_c = \varphi_c \rho/\rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry (DSC), (iii) mass density measurements, (iv) infrared spectroscopy (IR), (v) solid-state NMR spectroscopy, and (vi) vapor permeability. Unless stated otherwise, throughout this description a degree of crystallinity given for a polymer is expressed as a percentage (%) of crystallinity and expressed as a mass or volume fraction. Unless stated otherwise throughout this description a degree of crystallinity given for a polymer composition is expressed as a percentage (%) of crystallinity and expressed as a mass fraction.

Measurements of crystallinity may also be determined from a modified method of differential scanning calorimetry (DSC), e.g., over a temperature range of 30 Deg. C to 150 Deg. C., with modulation amplitude of 0.5° C. and heat rate of 6° C./minute and duration of 1 minute. Curves for reversible and irreversible heat flow were obtained. Normalized enthalpies of cold crystallization and re-crystallization may be calculated from exotherms visible on an irreversible heat flow curve, while normalized enthalpy of melting is obtained from integration of an endotherm on a reversible heat flow curve. For example, percentage crystallinity may be calculated using EQ. 1:

% Crystallinity=$(\Delta h1-(\Delta h2+\Delta h3))/(\Delta h4)$         EQ. 1.

Where

Δh1 is the enthalpy of melting;

Δh2 is the enthalpy of cold crystallization;

Δh3 is the enthalpy of recrystallization; and

Δh4 is the enthalpy of fusion for 100% crystalline material

A "stent" means a permanent, durable or non-degrading structure, usually comprised of a non-degrading metal or metal alloy structure, generally speaking, while a "scaffold" means a temporary structure comprising a bioresorbable or biodegradable polymer, metal or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. Crimping means a diameter reduction of a scaffold characterized by a significant plastic deformation of the scaffold. When the scaffold is deployed or expanded by the balloon, the inflated balloon plastically deforms the scaffold from its crimped diameter. Methods for crimping scaffolds made according to the disclosure are described in US20130255853.

"Recoil" means the response of a material following the plastic/inelastic deformation of the material. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility. The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate. Unless stated otherwise, values for "Tg" refer to an upper limit for Tg (E.g., for poly(L-lactide) and the Tg when the material is dry. Poly(L-lactide) has a glass transition temperature range of between about 55 to 60Deg. C. "Tg" for poly(L-lactide), for purposes of this disclosure, Tg is 60Deg. C.), or up to 65Deg. C. for a strain hardened tube. The glass transition temperature is a function of chain flexibility. The glass transition occurs when there is enough vibrational (thermal) energy in the system to create sufficient free-volume to permit sequences of 6-10 main-chain carbons to move together as a unit. At this point, the mechanical behavior of the polymer changes from rigid and brittle to tough and leathery.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

A "Solid Phase Process" or "Solid Phase Processing" means a process for strain-hardening a material using a die, where the plastic deformation of the material occurs at temperatures close to, and above the Tg of the material. "Close to, and above the Tg of the material" means the temperature of the material worked, and/or the die have temperatures of between about 10 to 30Deg. C. above the upper limit of Tg, about 15 to 25Deg. C. above the upper limit of Tg, about 10 to 20Deg. C. above the upper limit of Tg, or about 15 to 20Deg. C. above the upper limit of Tg. For example, for poly(L-lactide) (PLLA), which has an upper limit of Tg being about 60Deg. Celsius, or a blend of polylactide (PLA) and a PLA and polycaprolactone (PCL) random copolymer (20% PCL) and the blended PLA-PCL combination has between about 1% to 5% by weight PCL, which has about the same upper limit of Tg being about 60Deg. Celsius, the tube material and/or die has a temperature of about 70 to 90Deg. C., about 75 to 85 Deg. C, about 70 to 80Deg. C., or about 75 to 80Deg. C.

"Molecular weight" refers to either number average molecular weight (Mn) or weight average molecular weight (Mw). References to molecular weight (MW) herein refer to either Mn or Mw, unless otherwise specified. The Mn may be as measured by GPC-RI Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e. radial strength.

When the term "diameter" is used without specifying whether the diameter is an outer diameter or inner diameter (of a tube or scaffold), the term "diameter" shall mean the outer diameter, the inner diameter or the average between the inner and outer diameters.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. A scaffold or stent having a desired radial force can have an unacceptable crush recovery. And a scaffold or stent having a desired crush recovery can have an unacceptable radial force. Crush recovery and crush resistance aspects of scaffolds are described in greater detail in US20110190871. Crush recovery may be expressed with reference to the un-deformed diameter of the scaffold, e.g., an applied 25% crush and resulting 80% recovery means the scaffold when crushed (or pinched) by a magnitude equal to 25% of the scaffold's un-deformed diameter recovers up to only 80% of its un-deformed diameter after the crushing or pinching force is removed.

According to a first aspect of the invention there is disclosed a system and process for working a polymer material by die drawing. The polymer material, in the form of a tube, is pulled through a die to produce a drawn up and/or drawn down tube having an increased modulus.

FIGS. 1, 1A, 2A, and 2B show respective side, top and perspective views of components of a draw rig 10 adapted for performing a die drawing process according to the disclosure. The draw rig 10 may include a first portion 12 for heating and deforming a polymer tube 5 and a second portion 14 for pulling the tube 5 through the first portion at a designated draw speed.

Figure 2A:
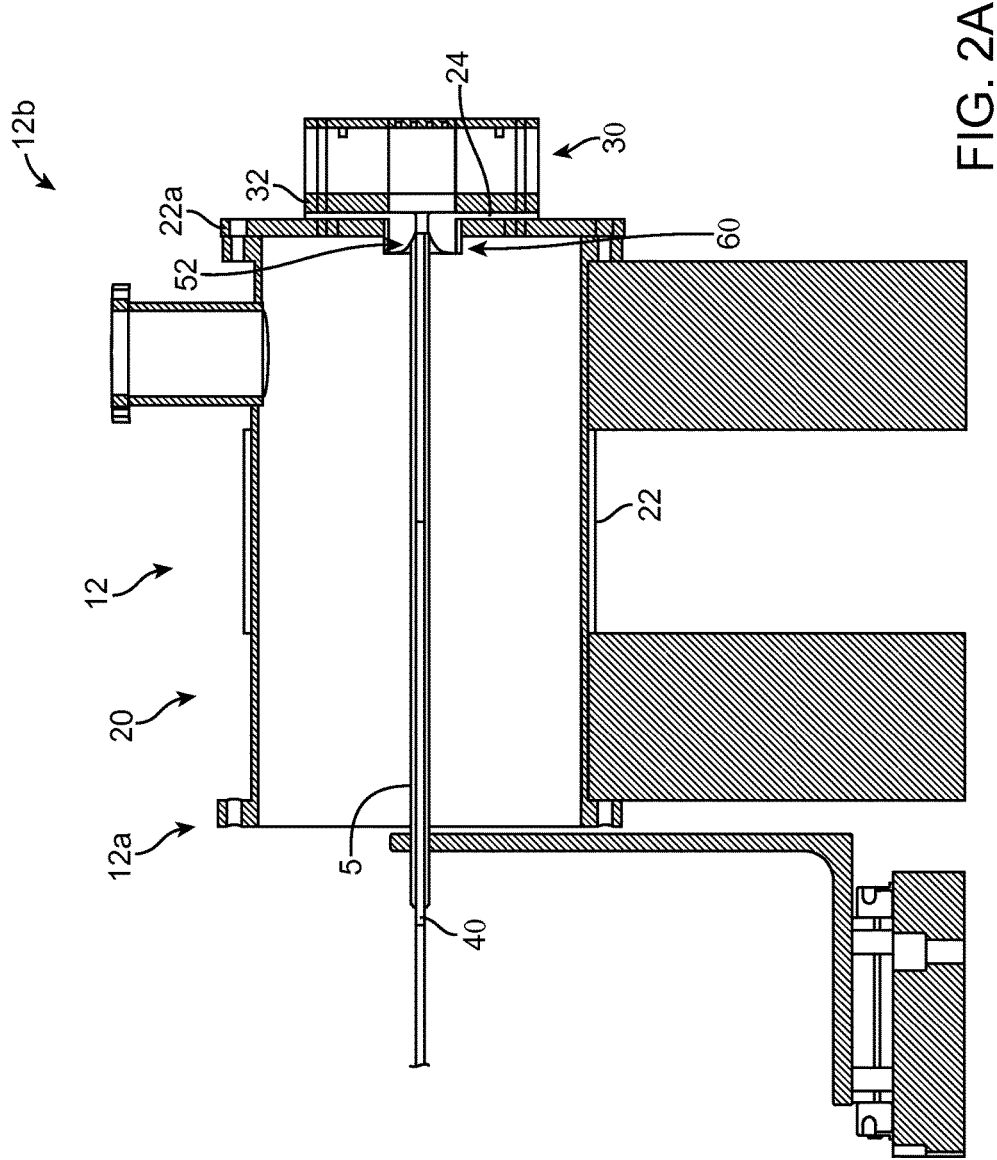
FIG. 2A is a cross-sectional side view, respectively, of the first portion of the apparatus of FIG. 1.

Referring to FIGS. 1A and 2A, the tube 5 passes through a cylindrical pre-heating chamber 20 before arriving at the die 60. The tube 5 enters the pre-heating chamber 20 from a round opening at an in-feed side or end 12a and exits from a round opening at an out-feed side or end 12b of a cooling chamber 30. The heating chamber 20 pre-heats the tube 5 to a pre-heat temperature (Tp). One or more band heaters 22 are used to maintain Tp within the chamber 20. A suitable pre-heat or dwell time before die drawing the tube is about 1 to 5, 1 to 20, or 10 to 100 seconds.

The cooling chamber 30 is configured to rapidly cool the drawn tube immediately after exiting the die. The cooling chamber is maintained at, or cools the exiting tube 5 to a quenching temperature (Tq) over a designated length, e.g., 25 mm, or time period, e.g., 1-5 seconds. The strain induced by the die aligns polymer chains. The cooling chamber rapidly cools this strain hardened piece exiting the die for the purpose of limiting any tendency for the polymer chains to return to a more random state of alignment while the tube has an elevated temperature.

The die 60 is part of a die plate 24, which can be interchanged with other die plates for purposes of changing from the die 60 (FIG. 3B) to another die, such as one of dies 50, 60, 70 and 80 (see FIGS. 3A-3D). The die plate 24 is secured to a heating plate 22a, which conducts heat to the die plate and maintains a die temperature (Td) while the tube is being pulled through the die 60.

An insulating ring 32 is disposed outside of the chamber 20 and between the heating ring 22a and the cooling chamber 30. The insulating ring 32 helps to thermally isolate the cooling chamber 30 from the heating plate 22a, so that the drawn tube 5 can be rapidly cooled down once it exits the die 60. The chamber 30 is connected to a cool air source (not shown) that provides a forced airflow onto the tube 5 exiting the die 60. In this sense the chamber 30 may be thought of as a mixing chamber.

According to some embodiments (as described in greater detail below) a mandrel or plug 40 is used during the draw process. The mandrel 40 is disposed within the pre-drawn tube 5. According to some embodiments the tube 5 is pressed between the mandrel 40 and inner walls of the die 60 to achieve the desired deformation characteristics. The mandrel 40 may be controlled by a server mechanism (not shown) which advances the mandrel towards and away from the die 60 and may apply a rotation to the mandrel 40, e.g., to help maintain a uniform temperature about the inner surface of the tube portions placed in contact with the mandrel 40.

Temperatures of the die 60, cooling chamber 30, pre-heating chamber 20 and mandrel 40 can be monitored using thermocouples (not shown).

Referring to FIG. 2B and FIG. 1, portion 14 includes a haul-away piece 14*a* including a tube gripper 18 that is linearly displaced over a servo-driven sled 14*b* at a draw speed. A load cell (not shown) is included to monitor the force required to maintain or arrive at the steady-state draw speed (Vd). The gripper 18 includes a 3-jaw pneumatic-activated piece 19 having a clamping force sufficient to hold the tube 5 in place without slippage.

According to some embodiments, including one or more of the Processes 1-5 discussed below, processing parameters for die drawing are provided in TABLE 1.

TABLE 1

Processing Parameters According to Some Embodiments

| | |
|---|---|
| Die Temperature (Td): | between about 10 and 35° C. above Tg of the polymer material. |
| Steady State Draw Speed (Vd): | between 0.1 mm/sec and 25 mm sec. |
| Incoming tube diameter (d1): | between about 0.09 and 0.5 inches. |
| Incoming tube wall thickness (t1) | between about .02 and .01 inches. |
| Die Taper angle (Θ) | between 15 and 60 degrees. |
| Pre-Heat Temperature (Tp) | about 5-10 degrees below Tg |
| Temperature difference between pre-heat chamber and die (Delta-Tin) | about 10 to 40° C. |
| Quench Temperature (Tq): | about 15 Deg. C. or temperature causing tube temperature to drop below 5-10 Deg. C. less than Tg within 1-2 sec from exiting die. Forced airflow into a cooling chamber (between about 5-10 Deg. C.) cools exit tube material to about 15° C. within 25 mm from exit of die. The forced air is between about 5 to 10° C. Alternatively, the chamber 30 may expose the outgoing tube to ambient air for cooling, i.e., no mixed or forced chilled air. |
| Temperature difference between die and chamber 30 (Delta-Tout) | about 50 to 80° C. |

According to some embodiments the incoming tube, i.e., the tube passed through the die, is a high molecular weight polymer composition. In a preferred embodiment the tube is a blend of polylactide (PLA) and a PLA and polycaprolactone (PCL) random copolymer (20% PCL) and the blended PLA-PCL combination has between about 1% to 5% by weight PCL. The number average molecular weight (Mn) of the PLA-PCL combination is 200 to 500 kDa or 300 to 500 kDa.

FIGS. 4A-4F shows embodiments of tubes processed according to one aspect of the disclosure. The dimensions provided under "Incoming Tube Dimensions" refer to the tube dimensions for tubes that are pulled through the die for four different processes. Incoming tube dimensions may refer to the dimensions after the tube is extruded and without blow-molding, or after the tube is blow-molded. Each process produces final tube outer diameters of 0.1365 inches, which is a preferred outer diameter. Inner diameter (or wall thickness) may vary slightly for a process. A summary of each of the processes follows.

PROCESS 1: an amorphous or substantially amorphous polymer tube is pulled through the die. No inner mandrel is used. See FIGS. 3A and 4A.

PROCESS 2: an expanded polymer tube is pulled through the die. No inner mandrel used. See FIGS. 3A and 4B.

PROCESS 3: an expanded polymer tube is pulled through the die. A flat or non-tapered mandrel is within the tube when the tube is passed through the die. See FIGS. 3B and 4C.

PROCESS 4: an expanded polymer tube is pulled through the die. A tapered mandrel is within the tube when the tube is passed through the die. The die has no taper. See FIGS. 3C and 4D.

PROCESS 5: an extruded/expanded tube is pulled through a die. A tapered mandrel is used. Both the die and mandrel radially expand the tube. The mandrel has a higher degree of taper than the die. See FIGS. 3E and 4E.

The dimensions provided under "Final Tube Dimensions" refer to the tube dimensions after being pulled through the die for each respective process. The "Draw Ratios" Ro and Ri refer to ratios of outer diameters and ratios of inner diameters, respectively, where Ro=outer diameter of incoming tube/outer diameter of final tube Ri=outer diameter of incoming tube/outer diameter of final tube The values for Ro vary from 2 to 4 for Process 1, 1.1 to 1.5 for Processes 2, 3 and 4 and 5 to 1.1 for Process 5.

FIGS. 3A-3E are cross-sectional views of dies that may be used in conjunction with the apparatus shown in FIGS. 1-2 and previously discussed. The die assemblies include a conical portion and/or tapered mandrel (or no mandrel at all), which plastically deforms the incoming tube to produce a strain-hardened tube. The conical portion is described by a die angle, taper angle, or taper (θ) and a length (Lc). Each of the dies may also have a cylindrical or flat land having a land length (Ll). The die length is (Lc+Ll). Upstream, or on the feed-side of the die, there is also preferably a support ring (not shown) that receives the incoming tube to maintain axial alignment of the tube as it enters and is pulled through the die.

The dies are used with the apparatus depicted in FIGS. 1-2 to perform the above-mentioned six processes, which are now discussed in more detail in connection with FIGS. 3A-3D.

In the following description accompanying each of the FIGS. 3A-3D, the following terms are used throughout. "Outgoing tube" refers to the portion of the tube 5 that has passed through the die and "Incoming tube" refers to the portion of the tube 5 that has yet to pass through the die. Additionally, the incoming tube has an outer diameter d1; the outgoing tube has a diameter d2; the incoming tube has a wall thickness t1 and the outgoing tube has a wall thickness t2.

Process 1

Figure 3A:
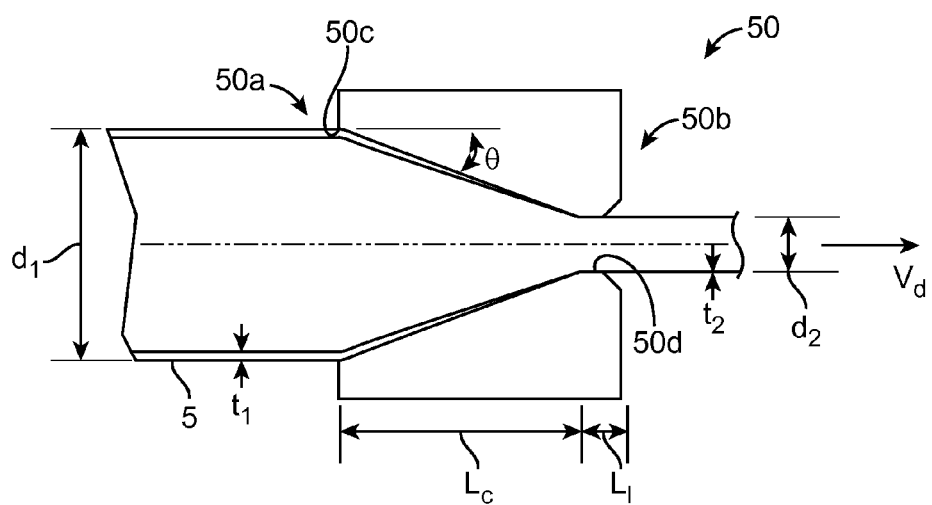
FIG. 3A is a first disclosure of a die for use with the apparatus of FIG. 1. A tube is being pulled through the die at the draw speed Vd.

PROCESS 1 is discussed further with frequent reference to FIG. 3A. There is shown a cross-sectional view of the tube 5 when deformed through a die 50. For this process the incoming tube 5 is an amorphous or substantially amorphous tube. For example, the incoming tube has less than 5% crystallinity, or not more than 1%, 2% or 4% crystallinity. A method for extruding such a tube is disclosed in US 2011/

0049751. It is believed that by using an amorphous tube the plastic deformation process of the die draw will produce a greater alignment and uniformity of the polymer chains.

The incoming diameter d1 is greater than d2 for Process 1. The die 50 is a draw down die such that the die opening at the outgoing end 50b is smaller than the die opening at the incoming end 50a. The die 50 has a land 50d. For the range in draw ratios given in FIG. 4A the die length Lc may be lengthened or shortened, or the die angle θ may be decreased or increased, respectively.

The tube 5 is preheated to Tp before arriving to the die 50. The surfaces of the die 50 have a temperature Td. The outer surface of the tube 5 makes contact with the die at die surface 50c, which refers to a conical ring section proximal end 50a. After coming into contact with conical ring surface 50c the tube begins to undergo a radial deformation.

When exiting the die 50 the outgoing tube 5 is strain hardened. In a preferred embodiment the tube 5, upon passing through end 50b, enters a cooling chamber (see chamber 30 in FIG. 1) that cools the strain hardened tube 5 either by exposure to ambient air or forced-air cooling. A rapid cooling or quenching step can help to maintain the orientated polymer chains induced in the tube material when the tube 5 was pulled through the die 50 at the elevated temperature Td.

For Process 1 Ro=Ri for each case and draw ratios range from 2 to 4. No mandrel is used for Process 1.

Process 2

The discussion above for Process 1 also applies equally to PROCESS 2, except that in Process 2 a blow-molded tube is used for the incoming tube 5. The blow-molded tube 5 has a biaxial alignment of polymer chains produced from a blow-molding process. The crystallinity of the blow-molded tube may range from 20 to 50%, 20 to 25%, 25 to 30%, 30 to 35%, 35 to 40%, 40 to 45%, and 45 to 50%. A suitable blow-molding process used to form the incoming tube is disclosed in US 2011/0066222 and below.

Process 3

Figure 3B:
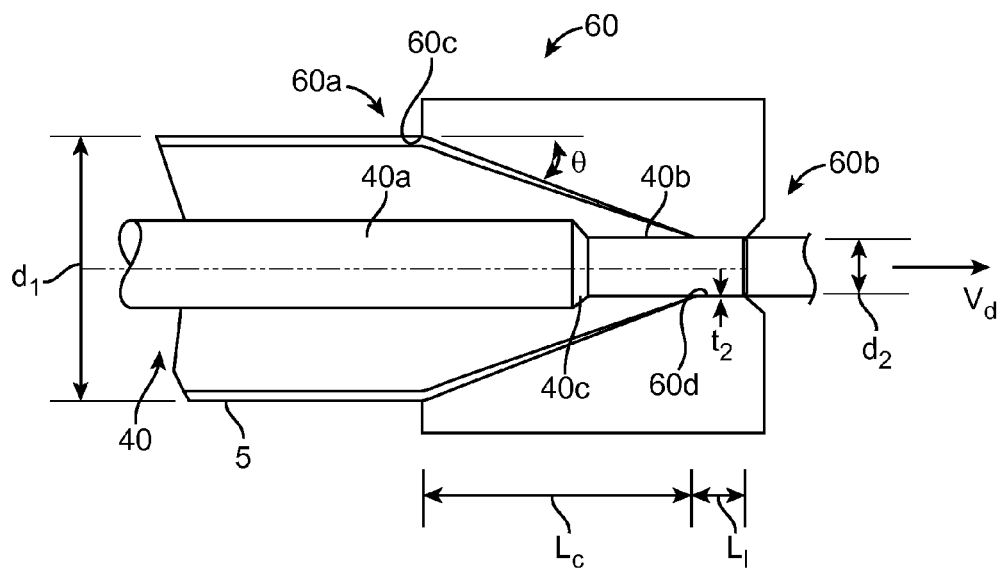
FIG. 3B is a second disclosure of a die for use with the apparatus of FIG. 1. A mandrel is used with the die of FIG. 3B during a die drawing process. A tube is being pulled through the die at the draw speed Vd.

PROCESS 3 is discussed with frequent reference to FIG. 3B. There is shown a cross-sectional view of the tube 5 when deformed through a die 60. For this process the incoming tube 5 is also a blow-molded tube 5. The tube 5 is pulled through the die 60 at a steady state draw speed Vd.

The incoming diameter d1 is greater than d2 for Process 3. The die 60 is a draw down die such that the die opening at the outgoing end 60b is smaller than the die opening at the incoming end 60a. The die 60 has a land 60d. The other features of the die 60, including the taper angle and length, heating and cooling temperatures and manner in which tube 5 is deformed by the die 60 is the same as described earlier in connection with FIG. 3A, except as described below.

The draw process described in FIG. 3B differs in one respect from the process described by FIG. 3A in that a mandrel 40 is used for Process 3, but not for Processes 1 and 2. The mandrel 40 used with die 60 includes a forward part 40b that is cylindrical or flat, i.e., no taper. A stepped section 40c separates section 40a and 40b. For Process 3 the stepped section 40c does not contribute to forming the tube 5. The outer diameter of part 40b is about equal to the desired inner diameter of the outgoing tube (FIG. 4C). The mandrel has a temperature of about Td. The mandrel 40 is rotated at a rate of between 1 and 25 revolutions per minute (rpm) during the draw to maintain a uniform temperature over the tube surface.

In some embodiments the clearance between mandrel 40 outer surface at section 40b and walls of the die 60 at land section 60d is such that the tube material is gently squeezed between the walls of the flat section 60d and surface 40b of the mandrel 40 when the tube 5 portion is pulled through the section 60d of the die 60. In other embodiments the clearance between the mandrel and wall surface at section 60d is such that the mandrel serves only the purpose of countering any necking behavior in the tube 5 and maintaining the desired outgoing diameters and/or wall thickness (FIG. 4B). Referring to FIG. 4C for Process 3 the draw ratios range from 1.1 to 1.5.

Process 4

Figure 3C:
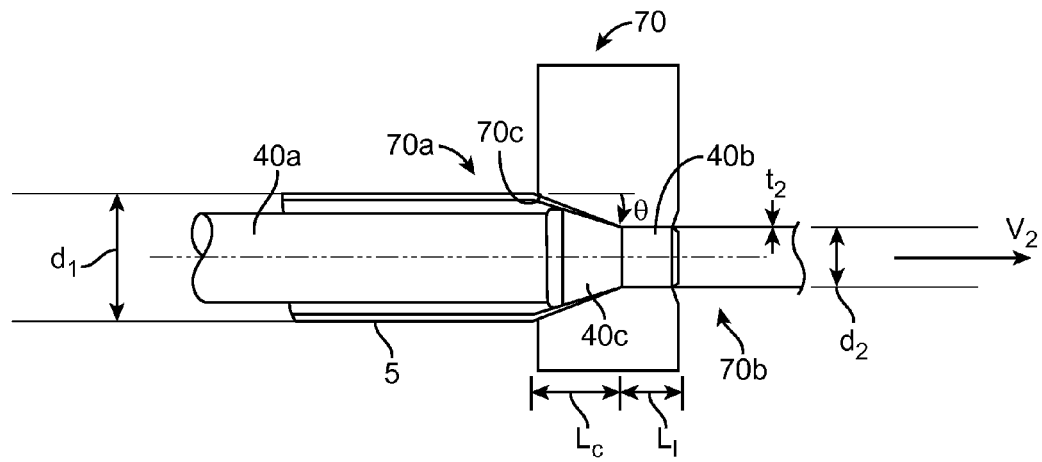
FIG. 3C is a third disclosure of a die for use with the apparatus of FIG. 1. A mandrel is used with the die of FIG. 3C during a die drawing process. A tube is being pulled through the die at the draw speed Vd.
Figure 3D:
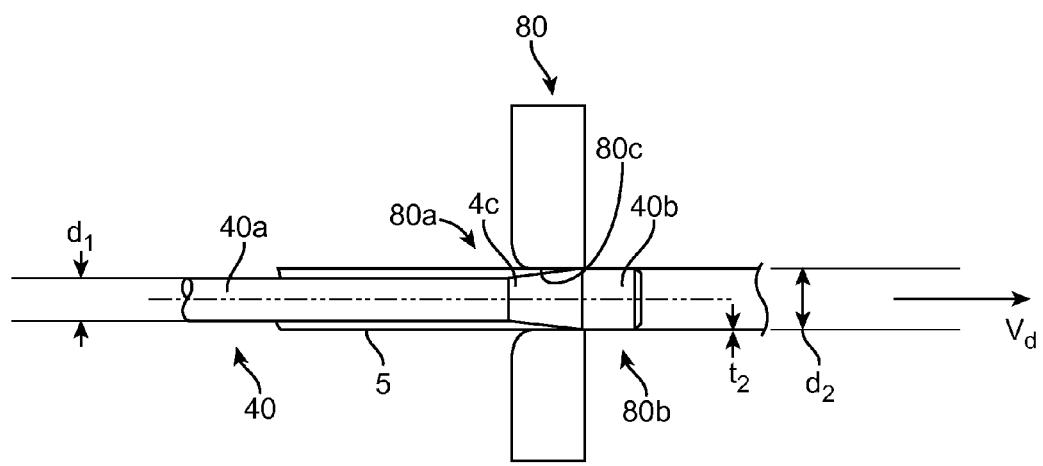
FIG. 3D is a fourth disclosure of a die for use with the apparatus of FIG. 1. A mandrel is used with the die of FIG. 3D during a die drawing process. A tube is being pulled through the die at a draw speed Vd.

PROCESS 4 is discussed further with reference to FIG. 3C. The description applies to Process 4 as just discussed in connection with Process 3, except that a tapered mandrel 40 is used for Process 4.

The incoming diameter d1 is greater than d2 for Process 4. The die 70 is a draw down die such that the die opening at the outgoing end 70b is smaller than the die opening at the incoming end 70a. The other features of the die 70, including the taper angle and length, heating and cooling temperatures and manner in which tube 5 is deformed by the die 70 is the same as described earlier in connection with FIGS. 3B and 3A, except that the stepped section 40c comes in contact with the tube 5, as illustrated in FIG. 3C.

The taper angle for section 40c may be between about 16 and 60 degrees. In some embodiments the taper angle for the section 40c may be less than, equal to, or about 5-10 Degrees less than the die angle θ for die 70. The function of the tapered section 40c and flat section 40b of the mandrel serves a similar purpose as that described earlier for the flat section 40b in connection with Process 3. For Process 4 the mandrel influences the deformed shape prior to the tube 5 exiting the conical section of the die 70. By utilizing a tapered mandrel in this fashion it is believed that an increased circumferential alignment of polymer chains across the thickness may be obtained by using the tapered mandrel in combination with the tapered walls of the die. Moreover, by using both the tapered mandrel and tapered die in contact with the tube there can be a more rapid equilibrium temperature reached, thereby enabling a reduced die length, which can be desired to limit the time period where the strain-hardened tube has a temperature above Tg. Referring to FIG. 4D, for Process 4 the draw ratios range from 1.1 to 1.5.

Process 5

Figure 3E:
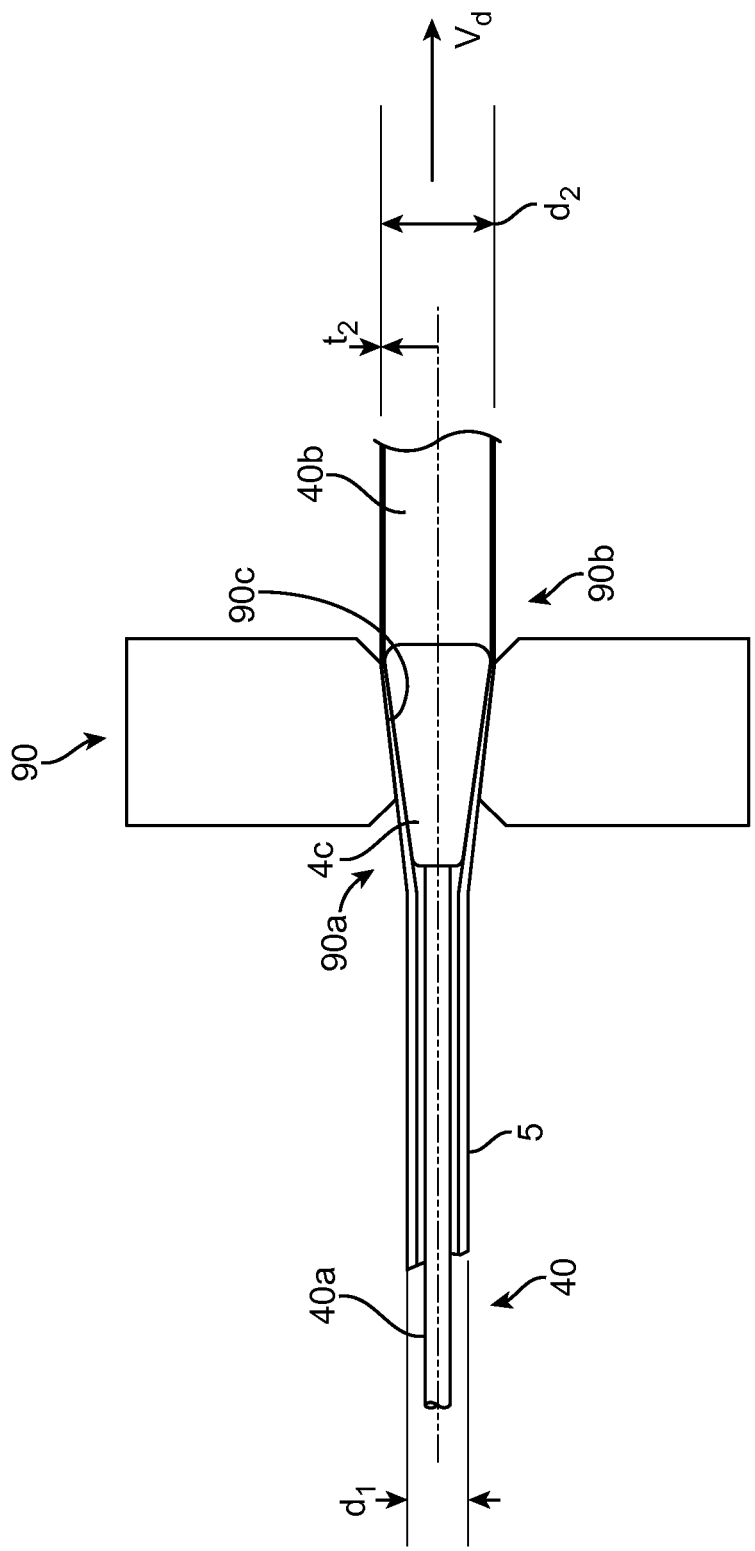
FIG. 3E is a fifth disclosure of a die for use with the apparatus of FIG. 1. A mandrel is used with the die of FIG. 3E during a die drawing process. A tube is being pulled through the die at a draw speed Vd.

PROCESS 5 is discussed further with reference to FIG. 3E. There is shown a cross-sectional view of the tube 5 when deformed through a die 90. For this process the incoming tube 5 is a blow-molded tube 5. The tube 5 is pulled through the die 90 at a steady state draw speed Vd. Preferably for Process 5 the feed tube 5 is an amorphous extruded tube. Alternatively the tube 5 may be an expanded tube, e.g., by blow-molding.

Both the incoming outer diameter d1 and the incoming inner diameter diameter d2 are increased for Process 5, but with the exception of two cases, their draw ratios are not equal. Referring to FIG. 4E, the inner draw ratio (Ri) is greater than the outer draw ratio (Ro) by a ratio of 5/1.4, 4/1.3, 3/1.2 and 2/1.2 respectively. To accomplish these different draw ratios the mandrel has a higher taper than the die. In an alternative embodiment Ro can be higher than Ri by approximately the same amount, by increasing the die taper and/or decreasing the mandrel taper.

The die 90 thus has taper. Its opening 90b is greater than 90a. The other features of the die 90, including the heating and cooling temperatures is the same as described earlier in connection with FIG. 3B, except as noted below.

A tapered mandrel 40 is used. In contrast to the mandrel 40 used for Process 3 and 4, the mandrel 40 for Process 5 is a diverging or draw up/out mandrel 40. The outer diameter of the section 40b disposed at the exit end 90b is greater than the diameter at the feed end 90a. A tapered section 40c extends through the feed-in end 90a of the die 90. The taper angle for the section 40c may range from about 10 or 16 to 60 degrees.

The clearance between mandrel 40 outer surfaces at 40c, 40d and walls 90c of the die 90 is such that the tube thickness is reduced gradually squeezed (in proportion to the mandrel section 40c taper) between the walls of the die 80 and surface of the mandrel 40 when the tube 5 portion is pulled through the die 80. This causes polymer chain orientation, as in the other Processes 1-4, but with an increase in the inner diameter and less in the outer diameter of the strain hardened tube 5 when it exits from the outgoing end 90b and optionally enters the cooling chamber 30.

Differential Axial/Radial Draw

According to any of the Processes 1-5 the die drawn tube may impose different degrees of axial orientation as the tube is being radially expanded. For example, for Process 5 the axial draw is 25% of the radial draw (with respect to either Ro or Ri the 25% refers; that is, the ratio of Ro or Ri to the axial draw yields 25%). The axial draw may alternatively be 10%, 20%, 30% or up to 50% of the radial draw.

In other embodiments, such as when the feed tube is a blow-molded tube, the axial draw may be different from the blow-molded tube and die drawn tube, by about 20%, 30%, 40%, 50% to 100%. For example, the blow-molded tube may have an axial draw that is only 10 to 20% of the radial draw. When the expanded tube is then die drawn the axial draw may be correspondingly greater, e.g., about 20, or 30-50% radial draw. This may then produce a strain hardened tube characterized by orientated polymer chains close to the outer or inner surface of the tube having a higher axial component of alignment verses polymer chains closer to the respective other inner and outer surfaces.

Figure 8:
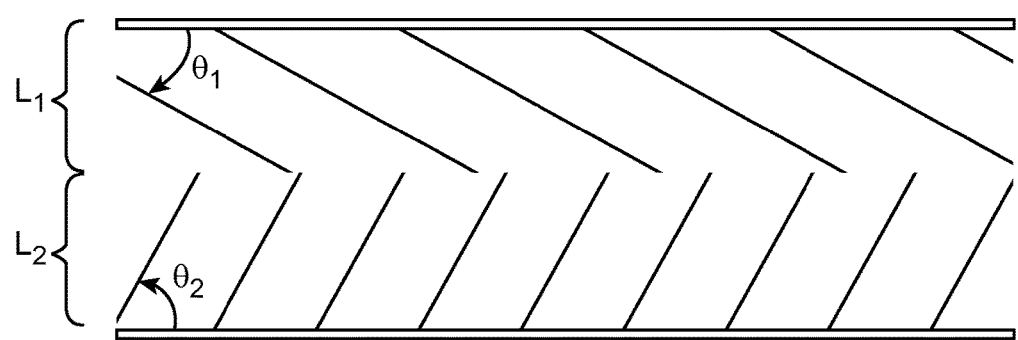
FIG. 8 shows a partial cross-section of a tube or scaffold showing an approximate orientation of polymer chains over the wall thickness.

This aspect of the disclosure is illustrated in FIG. 8. The lines and angles θ1 and θ2 indicate the orientation of polymer chains in the material (following strain hardening) over the wall thickness of a tube (or scaffold) according to the disclosure. θ1 and θ2 indicate a resultant orientation for polymer chains after the tube was processed by a first and second strain hardening process, e.g., blow-molding followed by die-drawing. Both were biaxial expansion (or contraction processes). The first process produces substantially the orientation shown in L2, followed by the second process, which produces the orientation shown in layer L1.

Blow Molding

With reference to FIGS. 5A-5D there is described a blow-molding process for producing the incoming tubes for Processes 2-5. The blow molding process is the same as described in US 2011/0066222.

Figure 5A:
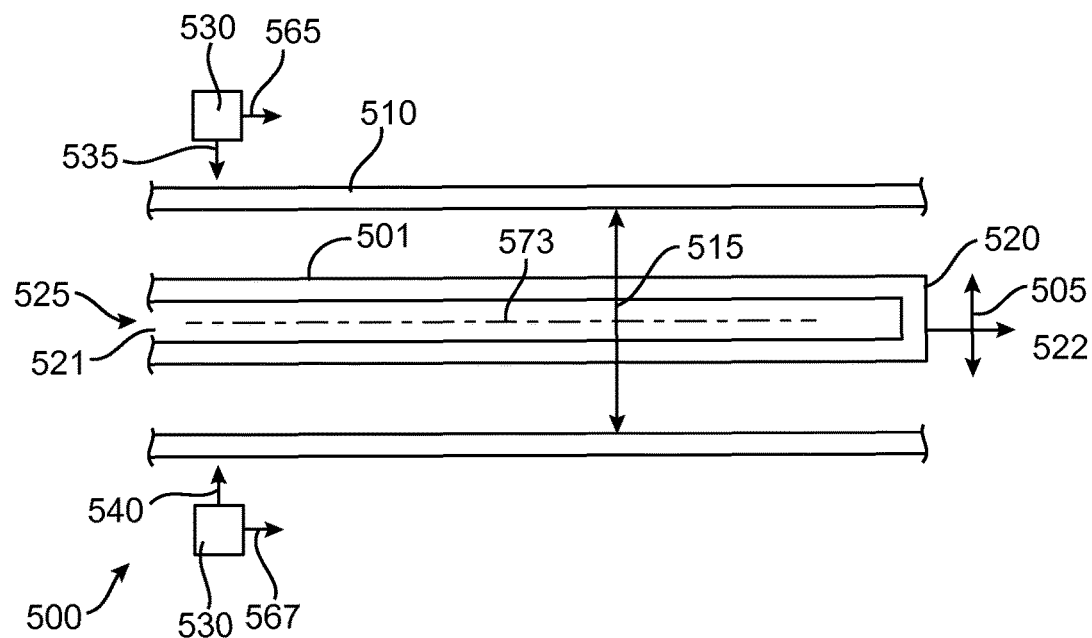
FIGS. 5A-5D show aspects of a blow-molding process for biaxially expanding a tube.
Figure 5B:
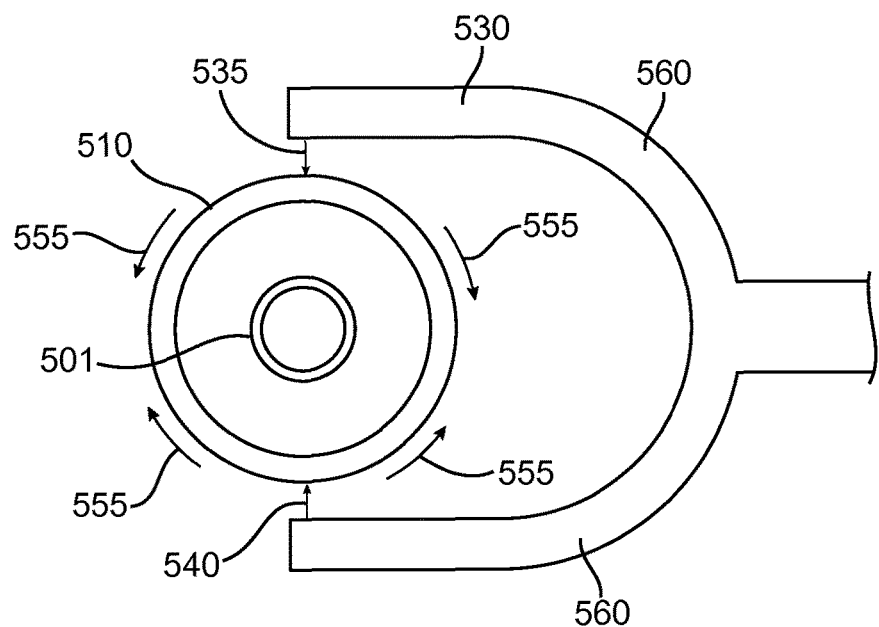
Figure 5C:
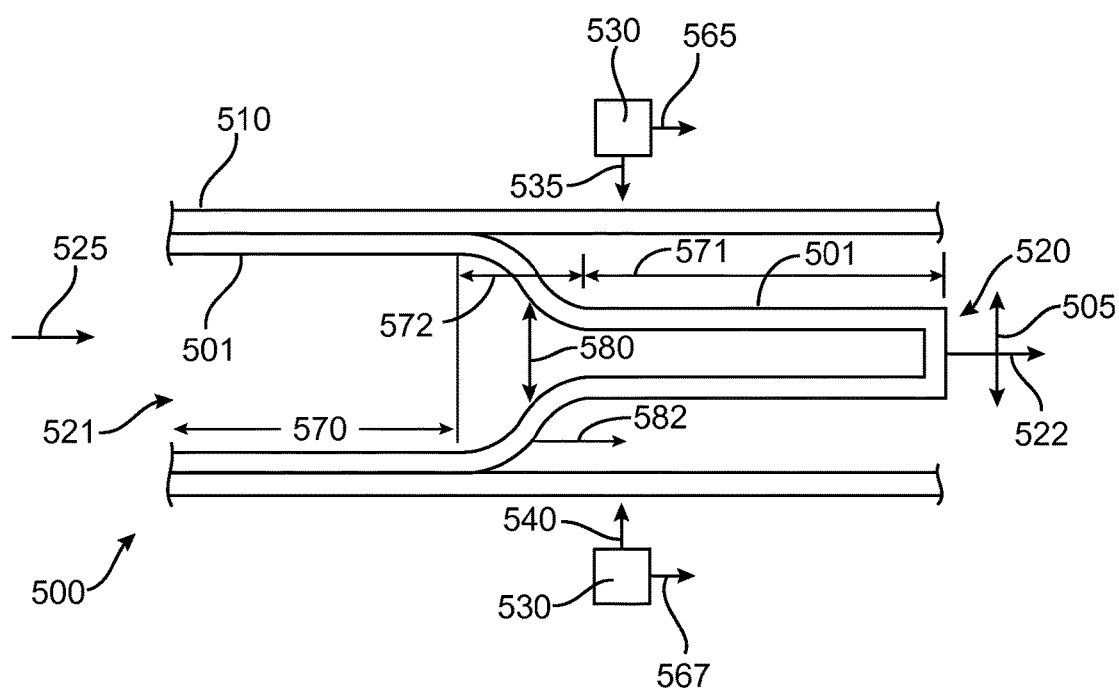
Figure 5D:
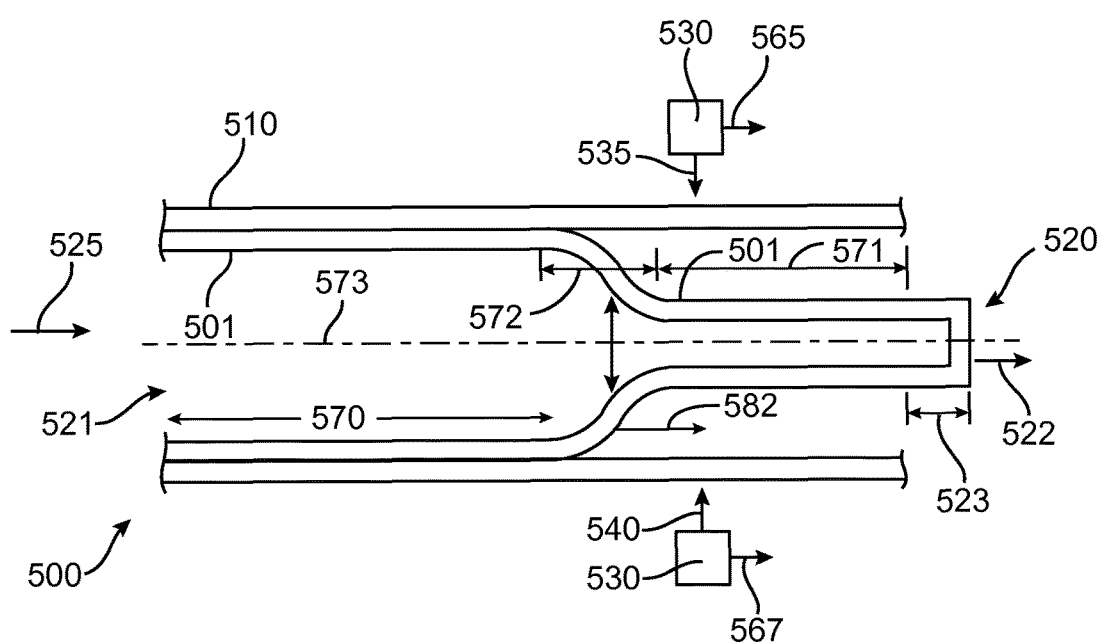

FIGS. 5A-5D schematically depicts a molding system 500 for simultaneous radial and axial deformation of a polymer tube. FIG. 5A depicts an axial cross-section of a polymer tube 501 with an un-deformed outside diameter 505 positioned within a mold 510. The mold 510 limits the radial deformation of the polymer tube 501 to a diameter 515 corresponding to the inside diameter of the mold 510. The polymer tube 501 is closed at a distal end 520. A gas is conveyed, as indicated by an arrow 525, into an open end 521 of the polymer tube 501 to increase internal fluid pressure within tube 501. A tensile force 522 is applied to the distal end 520 in an axial direction. In other embodiments, a tensile force is applied at the proximal end 521 and the distal end 520. A circular band or segment of the polymer tube 500 is heated by a nozzle 550. The nozzle has fluid ports that direct a heated fluid, such as hot air, at two circumferential locations of the mold 510, as shown by arrows 555 and 540. In another embodiment a laser is used to heat the tube. FIG. 5B depicts a radial cross-section showing the tube 501 within the mold 510, and the nozzle 550 supported by structural members 560. Additional fluid ports can be positioned at other circumferential locations of the mold 510 to facilitate uniform heating around a circumference of the mold 510 and the tube 501. The heated fluid flows around the mold 510, as shown by arrows 555, to heat the mold 510 and the tube 501 to a predetermined temperature above ambient temperature. The nozzle 550 translates along the longitudinal axis 575 of the mold 510 as shown by arrows 565 and 567. That is, the nozzle 550 moves linearly in a direction parallel to the longitudinal axis 575 of the mold 510. As the nozzle 550 translates along the axis of the mold 510, the tube 501 radially deforms. The combination of elevated temperature of the tube 501, the applied axial tension, and the applied internal pressure cause simultaneous axial and radial deformation of the tube 501, as depicted in FIGS. 5C and 5D.

FIG. 5C depicts the system 500 with an undeformed section 571, a deforming section 572, and a deformed section 570 of the polymer tube 501. Each section 570, 571, 572 is circular in the sense that each section extends completely around the central axis 575. The deforming section 572 is in the process of deforming in a radial direction, as shown by arrow 580, and in an axial direction, as shown by arrow 582. The deformed section 570 has already been deformed and has an outside diameter that is the same as the inside diameter of the mold 510.

FIG. 5D depicts the system 500 at some time period after FIG. 5C. The deforming section 572 in FIG. 5D is located over a portion of what was an un-deformed section in FIG. 5C. Also, the deformed section 570 in FIG. 5D is located over what was the deforming section 572 in FIG. 5C. Thus it will be appreciated that the deforming section 572 propagates linearly along the longitudinal axis 575 in the same general direction 565, 567 that the heat sources 550 are moving.

In FIG. 5D, the deforming section 572 has propagated or shifted by an axial distance 574 from its former position in FIG. 5D. The deformed section 570 has grown longer by the same axial distance 574. Deformation of the tube 501 occurs progressively at a selected longitudinal rate along the longitudinal axis 575 of the tube. Also, the tube 501 has increased in length by a distance 525 compared to FIG. 5C.

Depending on other processing parameters, the speed at which the heat sources or nozzles 550 are linearly translated over the mold 510 may correspond to the longitudinal rate of propagation (also referred to as the axial propagation rate) of the polymer tube 501. Thus, the distance 574 that the heat sources 550 have moved is the same distance 575 that the deformed section 570 has lengthened.

The rate or speed at which the nozzles 550 are linearly translated over the mold 510 is a processing parameter that relates to the amount of time a segment of the polymer tube is heated at the expansion temperature and the uniformity of such heating in the polymer tube segment.

In some embodiments an extruded tube prior to blow-molding is amorphous or substantially amorphous having a crystallinity of no greater than 5%. The blow molding, in preferred embodiments, imposes RE and AE ratios of between 400% and 500%, preferably about 450% and 40-50%, respectively. The ratios are defined in US 2011/

0066222. The temperature for blow molding is preferably between about 10° C. and 60° C. above the Tg of the polymer material, or more preferably between about 20° C. and 30° C. above the Tg of the polymer material. The temperature is chosen sufficiently above Tg so that the tube gains stiffness and strength benefits from the biaxial expansion while limiting brittle behavior.

A polymer scaffold according to a preferred embodiment is formed from a radially expanded or biaxially expanded extruded PLLA tube. The degree of radial expansion (RE) and axial expansion (AE) that the polymer tube undergoes can characterize the degree of induced circumferential molecular and crystal orientation as well as strength in a circumferential direction. In some embodiments the RE is about 400% and the AE is 40-50%.

Other embodiments of processing parameters, RE and AE expansions considered within the scope of the disclosure are found in U.S. application Ser. No. 13/840,257 filed Mar. 15, 2013. In particular, in some embodiments there is a blow-molding process wherein biaxial expansion ranges from about 400-500 in the radial direction and from about 150-200 in the axial direction; and the ratio RE/AE may be between about 2 and 1, 2.5 to 1, 3 to 1, and 4 to 1. Ratios of 2.5 to 1 or 2 to 1 may be preferred to limit recoil of the scaffold.

Material (Other Embodiments)

As mentioned earlier, according to some embodiments the incoming tube, i.e., the tube passed through the die, is a high molecular weight polymer composition. In a preferred embodiment the tube is a blend of polylactide (PLA) and a PLA and polycaprolactone (PCL) random copolymer (20% PCL) and the blended PLA-PCL combination has between about 1% to 5% by weight PCL.

Other polymer combinations are contemplated. Among the combinations: (1) PLA and PCL random copolymer; (2) block copolymer including PLA polymer blocks and PCL polymer blocks; (3) a blend of a PLA polymer with PCL homopolymer; (4) blend of a PLA homopolymer blended and a PLA and PCL copolymer; and (5) a blend of a PCL homopolymer and a PLA and PCL copolymer.

The incoming tube may be made substantially or completely of the polymer combination. "Substantially" in this context means greater than 90 wt %, greater than 95 wt %, or greater than 99 wt %. The incoming tube may have a composition of 90 to 95% or 95 to 99% of the polymer combination. The PLA polymer of the combination may include poly(L-lactide) (PLLA), poly(D,L-lactide) having a constitutional unit weight-to-weight (wt/wt) ratio of about 96/4, poly(lactide-co-glycolide), poly(L-lactide-co-glycolide), poly(D,L-lactide-co-glycolide), poly(D,L-lactide) made from meso-lactide, and poly(D,L-lactide) made from polymerization of a racemic mixture of L- and D-lactides. A PLA polymer can include a PLA with a D-lactide content greater than 0 mol % and less than 15 mol %, or more narrowly, 1 to 15 mol %, 1 to 5 mol %, 5 to 10%, or 10 to 15 mol %. The PLA polymer includes poly(D,L-lactide) having a constitutional unit weight-to-weight (wt/wt) ratio of about 93/7, about 94/6, about 95/5, about 96/4, about 97/3, about 98/2, or about 99/1. The term "unit" or "constitutional unit" refers to the composition of a monomer as it appears in a polymer.

The incoming tube may include a PLA and PCL random copolymer. The tube may be made substantially or completely of the copolymer. The copolymer may include poly(L-lactide-co-caprolactone), poly(D,L-lactide-co-caprolactone), poly(L-lactide-co-glycolide-co-caprolactone), and poly(DL-lactide-co-glycolide-co-caprolactone). The copolymer with D,L-lactide may be made from a racemic mixture of L- and D-lactide or may include 1 to 15% of D constitutional units. The tube may be made substantially or completely of the copolymer. In some embodiments, the tube may include no PLA homopolymer, PCL homopolymer, or less than 20%, 10%, 5%, or less than 1% of either homopolymer.

The copolymer may include 1 to 5% (wt % or mol %) of caprolactone units, or more narrowly, 1 to 2%, 2 to 5%, 3 to 5%, or about 3%. The tube may be made from a copolymer resin with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the copolymer or tube made of the copolymer and following blow molding or die drawing may be 20 to 50%, 20 to 25%, 25 to 30%, 30 to 35%, 35 to 40%, 40 to 45%, and 45 to 50%.

Embodiments of a die drawn tube include tubes that are a block copolymer including PLA polymer blocks and PCL polymer blocks. The tube may be made substantially or completely of the block copolymer. The block copolymer may be a linear block copolymer or branched block copolymer such as a star block copolymer.

The tube may include no PLA homopolymer, PCL homopolymer, or less than 20%, 10%, 5%, or less than 1% of either homopolymer. The PLA blocks may include PLLA, poly(L-lactide-co-glycolide), poly(D,L-lactide-co-glycolide), and poly(D,L-lactide). Blocks with D,L-lactide may be made from a racemic mixture of L- and D-lactide or may include 1 to 15% of D constitutional units. The tube may be made substantially or completely of the block copolymer.

The block copolymer may include 1 to 5% (wt % or mol %) of polycaprolactone blocks, or more narrowly, 1 to 2%, 2 to 5%, 3 to 5%, or about 3%. The tube may be made from a copolymer resin with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the copolymer or tube made of the copolymer after blow molding or die drawing may be 20 to 50%, 20 to 25%, 25 to 30%, 30 to 35%, 35 to 40%, 40 to 45%, and 45 to 50%.

Embodiments of a die drawn tube include tubes that are a blend of a PLA polymer with a PCL homopolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units. The tube may be made substantially or completely of the block copolymer.

The blend may include 1 to 5% (wt % or mol %) of PCL homopolymer, or more narrowly, 1 to 2%, 2 to 5%, 3 to 5%, or about 3%. The tube may be made from a PLA resin or resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a die drawn tube include tubes that are a blend of a PLA polymer with a PLA and PCL copolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units.

The copolymer may be PLA and PCL random copolymer or a block copolymer of PLA polymer blocks and PCL homopolymer blocks. The random copolymer may include any from the list of PLA and PCL random copolymers provided above. The block copolymer may be linear block copolymer or branched block copolymer such as a star block copolymer. The tube may be made substantially or completely of the blend.

The tube may be made from a PLA resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The caprolactone units in either the random or block copolymer may be 1 to 5% (wt % or mol %) of the blend, or more narrowly, 1 to 2%, 2 to 5%, 3 to 5%, or about 3% of the blend.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a die drawn tube include tubes that are a blend of a PCL homopolymer with a PLA and PCL copolymer. The tube may be made substantially or completely of the blend. The copolymer may be PLA and PCL random copolymer or a block copolymer of PLA polymer blocks and PCL homopolymer blocks. The random copolymer may include any from the list of PLA and PCL random copolymers provided above. The block copolymer may include any from the list of PLA and PCL block copolymers provided above. The block copolymer may be linear block copolymer or branched block copolymer such as a star block copolymer. The tube may be made substantially or completely of the blend.

The tube may be made from a copolymer resin or the resin blend with an IV greater than 5 dL/g, greater than 7 dL/g greater than 8 dl/g, 4 to 8 dL/g, 4 to 6 dL/g, 6 to 8 dL/g, or 5 to 7 dL/g.

The total caprolactone units in both the copolymer and the PCL may be 1 to 5% (wt % or mol %) of the blend, or more narrowly, 1 to 2%, 2 to 5%, 3 to 5%, or about 3% of the blend. The PCL homopolymer may be 0.5% to 4% of the blend. The caprolactone content of the copolymer may be 05% to 4%.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Scaffold Examples

Examples of scaffolds made from tubes according to the disclosure follow with reference to FIGS. 6, 6A, 7 and 7A.

Figure 6:
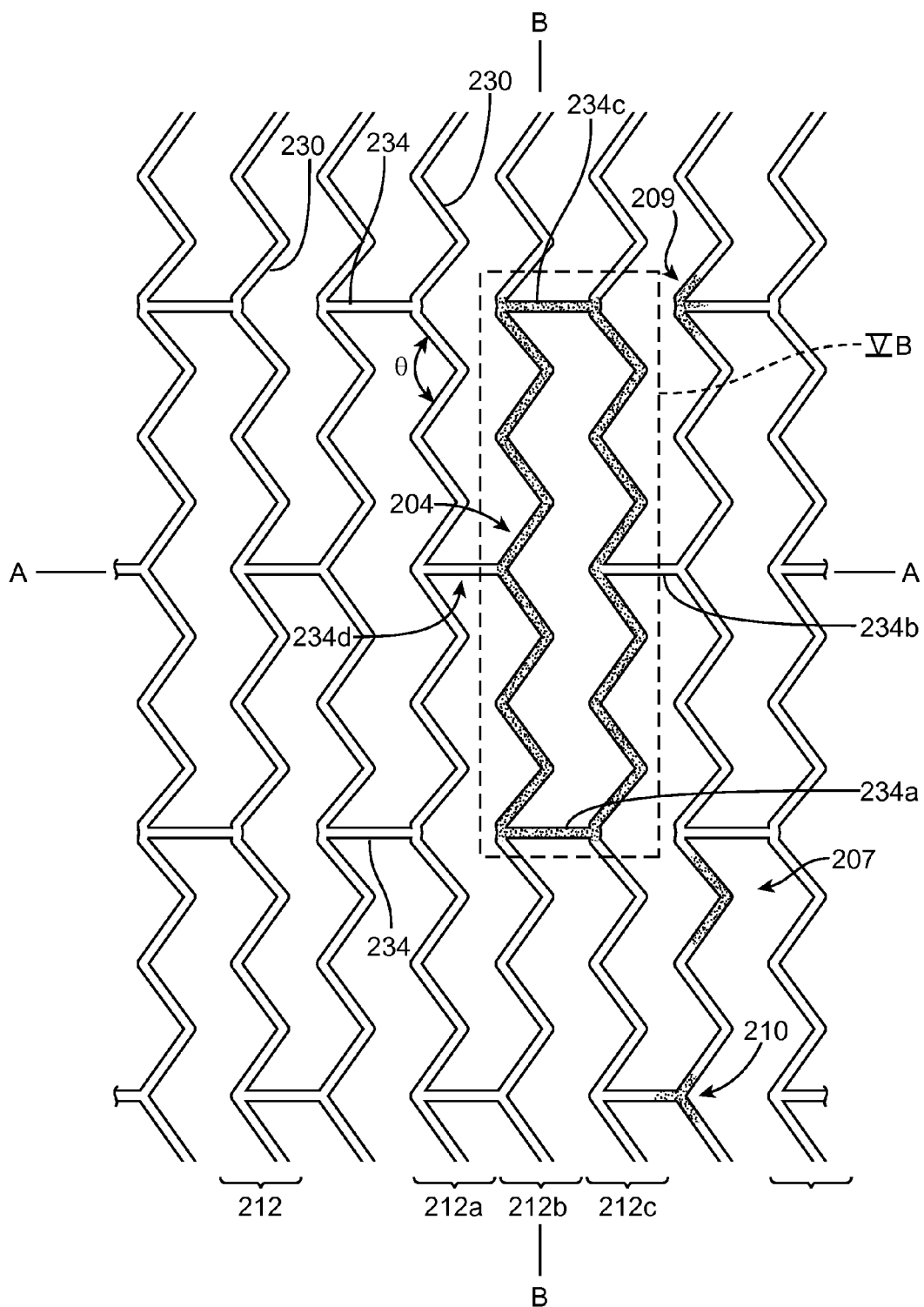
FIGS. 6 and 6A show aspects of a first scaffold pattern for a scaffold made from a tube processed in accordance with the disclosure.

Referring to FIG. 6, a scaffold pattern 200 includes longitudinally-spaced rings 212 formed by struts 230. There are eight crowns or crests formed by the struts. A ring 212 is connected to an adjacent ring by no more than two links 234, each of which extends parallel to axis A-A. In this first embodiment of a scaffold pattern (pattern 200) two links 234 connect the interior ring 212, which refers to a ring having a ring to its left and right in FIG. 2, to each of the two adjacent rings. Thus, ring 212b is connected by two links 234 to ring 212c and two links 234 to ring 212a. An end ring (not shown) is an end ring connected to only one other ring.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200. As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 6). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than, or equal to a maximum expanded scaffold diameter that the delivery balloon can, or is capable of producing when inflated.

Figure 7:
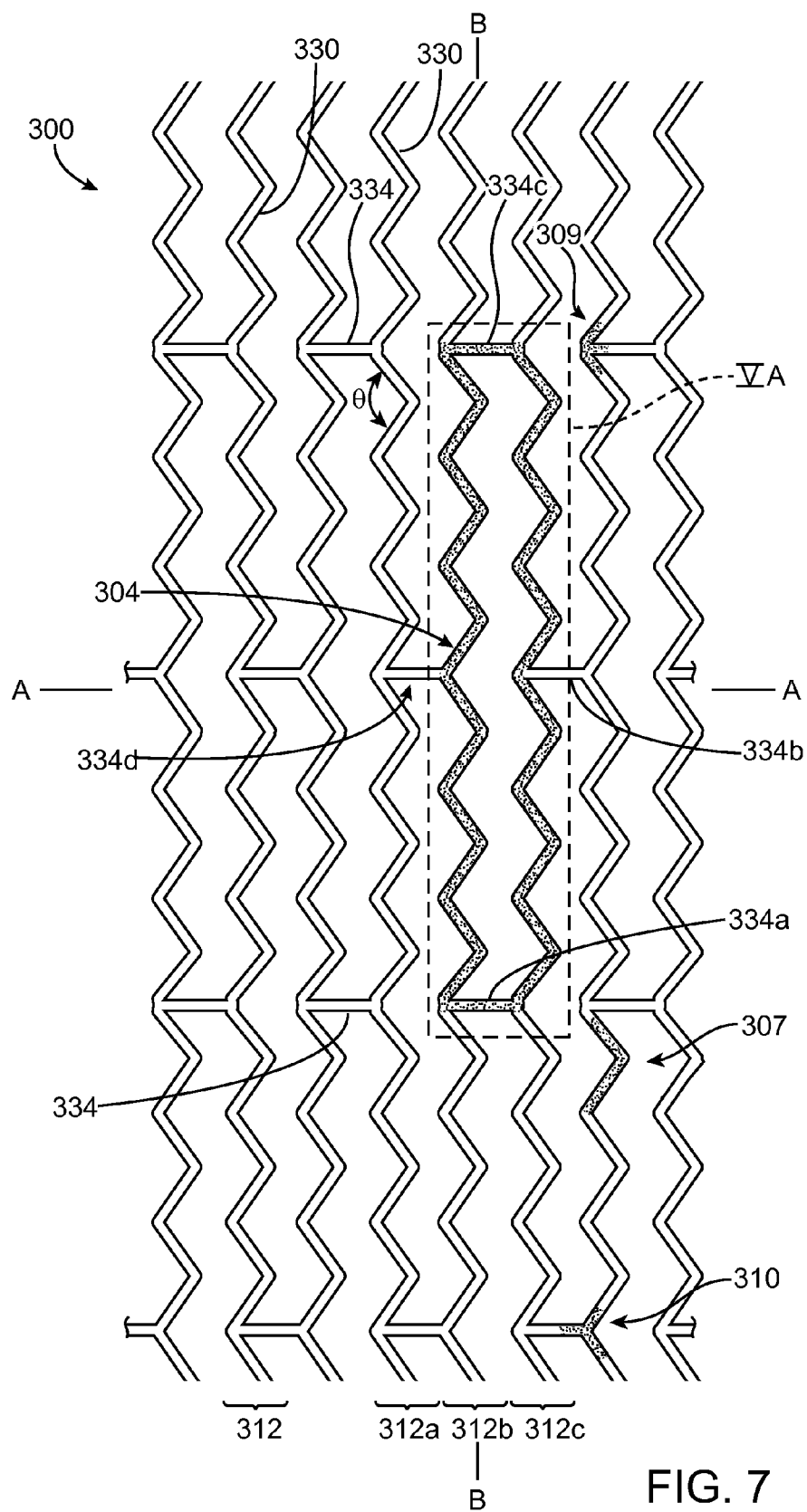
FIGS. 7 and 7A show aspects of a first scaffold pattern for a scaffold made from a tube processed in accordance with the disclosure.

A second embodiment of a scaffold structure has the pattern 300 illustrated in FIG. 7. Like the pattern 200, the pattern 300 includes longitudinally-spaced rings 312 formed by struts 330. There are twelve crests or crowns formed by the struts for each ring 312. A ring 312 is connected to an adjacent ring by no more than two links 334, each of which extends parallel to axis A-A. The description of the structure associated with rings 212, struts 230, links 234, and crowns 207, 209, 210 in connection with FIG. 6, above, also applies to the respective rings 312, struts 330, links 334 and crowns 307, 309 and 310 of the second embodiment, except that in the second embodiment there are 12, as opposed to 8 crests or crowns for each ring 312 for pattern 300.

Figure 6A:
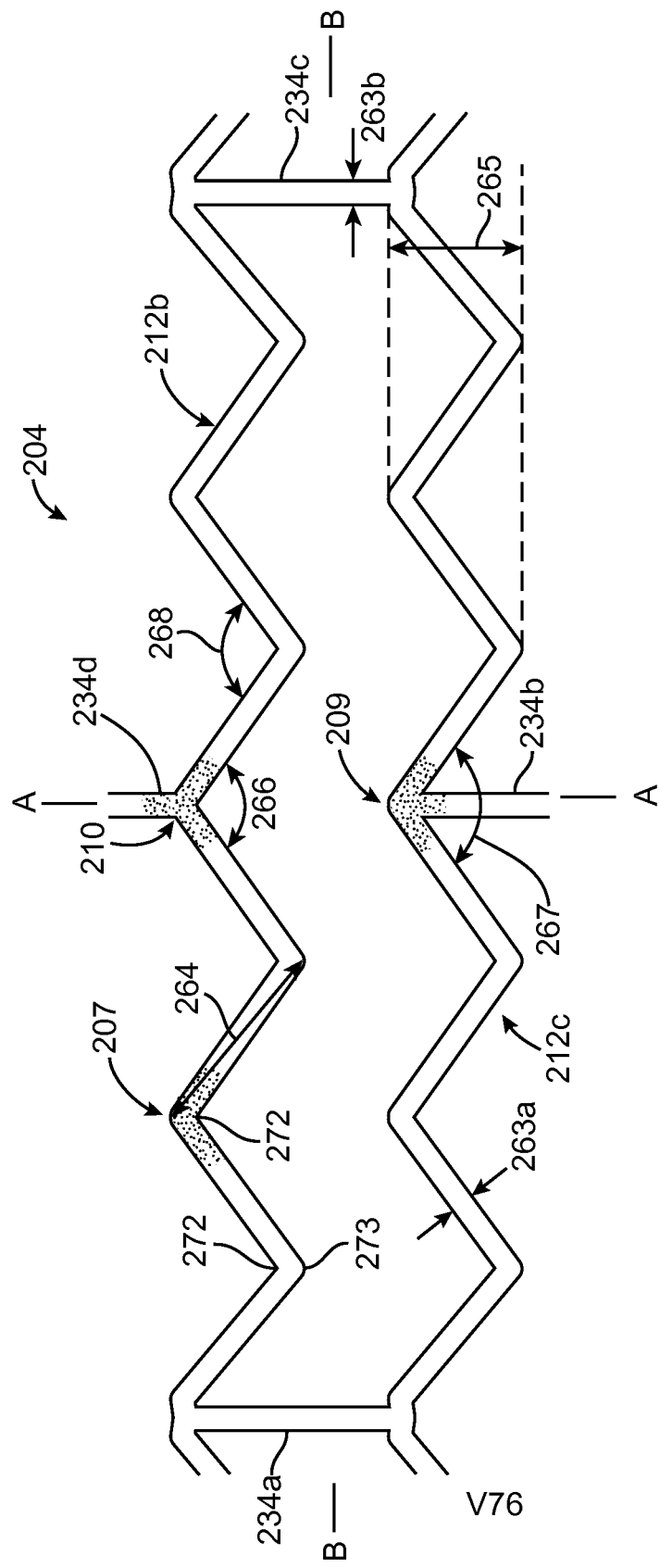
Figure 7A:
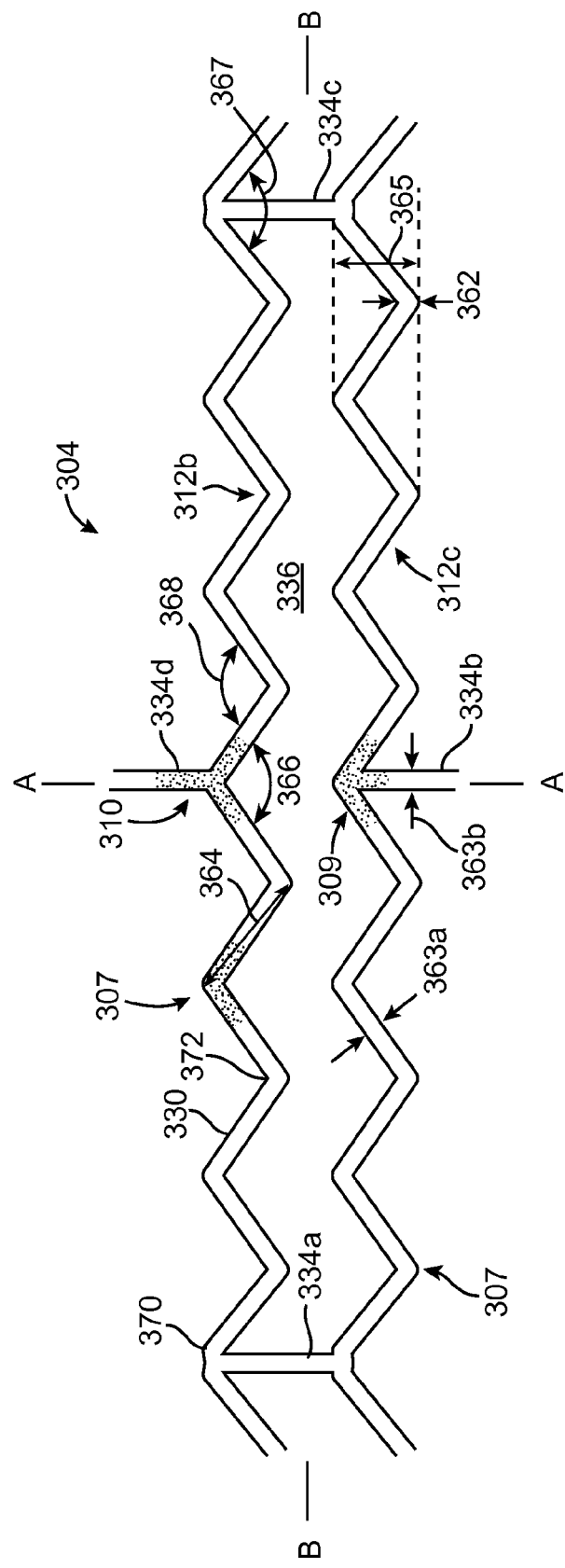

FIGS. 7A and 6A depict aspects of the repeating pattern of closed cell elements associated with each of the patterns 300 and 200, respectively. FIG. 7A shows the portion of pattern 300 bounded by the phantom box VA and FIG. 6A shows the portion of pattern 200 bounded by the phantom box VB. Therein are shown cell 304 and cell 204, respectively. In FIGS. 6A, 7A the vertical axis reference is indicated by the axis B-B and the longitudinal axis A-A. There are two such cells 204 formed by each pair of rings 212 in pattern 200, e.g., two cells 204 are formed by rings 212b and 212c and the links 234 connecting this ring pair, another two cells 204 are formed by rings 212a and 212b and the links connecting this ring pair, etc. Similarly, there are two cells 304 formed by rings 312b and 312c and the links 334 connecting this ring pair, another two cells 304 are formed by rings 312a and 312b and the links connecting this ring pair, etc.

Referring to FIG. 7A, the space 336 of cell 304 is bounded by the longitudinally spaced rings 312b and 312c portions shown, and the circumferentially spaced and parallel links 334a and 334c connecting rings 312b and 312c. Links 334b and 334d extend parallel to each other and connect the cell 304 to the right and left adjacent ring in FIG. 7, respectively. Link 334b connects to cell 304 at a W-crown 309. Link 334d connects to cell 304 at a Y-crown 310. A "W-crown" refers to a crown where the angle extending between a strut 330 and the link 336 at the crown 310 is an acute angle (less than 90 degrees). A "Y-crown" refers to a crown where the angle extending between a strut 330 and the link 334 at the crown 309 is an obtuse angle (greater than 90 degrees). The same definitions for Y-crown and W-crown also apply to the cell 204. There are eight unconnected or "U-crowns" 307 for cell 304, which may be understood as eight crowns devoid of a link 334 connected at the crown. There are always two U-crowns between a Y-crown or W-crown for the cell 304.

Additional aspects of the cell 304 of FIG. 7A include angles for the respective crowns 307, 309 and 310. For the scaffold having the pattern 300 the struts 330 have strut widths 363 and strut lengths 364, and the links 334 have link widths 363. Each of the rings 312 has a ring height 365. The radii at the crowns are, in general, not equal to each other. Cell 304 of pattern 300 may be regarded as a symmetric cell, by virtue of it always having two U-crowns on each side of a W-crown and Y-crown as shown.

Referring to FIG. 6A, the space 236 of cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 6, respectively. Link 234b connects to cell 236 at a W-crown 209. Link 234d connects to cell 236 at a Y-crown 210. There are four crowns 207 for cell 204, which may be understood as four crowns devoid of a link 234 connected at the crown. Cell 204 may also be regarded as a symmetric cell, by virtue of it always having one U-crown on each side of a W-crown and Y-crown as shown.

Additional aspects of the cell 204 of FIG. 6A include angles for the respective crowns 207, 209 and 210. Those angles are identified in FIG. 6A as angles 267, 269 and 268, respectively associated with crowns 207, 209 and 210. For the scaffold having the pattern 200 the struts 230 have strut widths 263a and strut lengths 264, the crowns 207, 209, 210 have crown widths 270, and the links 234 have link widths 263b. Each of the rings 212 has a ring height 265. The radii of the crowns are identified in FIG. 7A as inner radii 272 and outer radii 273.

The patterns 200 and 300 both have a symmetric cell design. A "symmetric" cell design (as shown in FIGS. 7A and 6A) has an equal number of U-crowns on each side of a W-crown or Y-crown. An example of an asymmetric cell design would be the V23 scaffold pattern, as described in US2011/0190871.

A significant difference between the pattern 300 and 200 is that the pattern 200 (as well as other designs, described below) has eight crowns and two links whereas the pattern 300 design has twelve crowns and two links. Having more crowns and therefore shorter bar arms than other designs, the pattern 300 has a higher density of struts.

TABLE 2 provides a summary of the characteristics of various scaffolds that may be made from tubes processed according to the disclosure. The patterns of the scaffolds can be appreciated in view of the TABLE 2 data taken with FIGS. 6-7 and accompanying description.

TABLE 2

| Wall thickness (microns) | Tube OD (mm) | Number of crowns | Links connecting adjacent rings |
|---|---|---|---|
| 150-190 | 7 | 9 | 3 |
| 150-190 | 7 | 9 | 3 |
| 150-190 | 9 | 9 | 3 |

TABLE 2-continued

| Wall thickness (microns) | Tube OD (mm) | Number of crowns | Links connecting adjacent rings |
|---|---|---|---|
| 150-190 | 8 | 8 | 4 |
| 150-190 | 7 | 9 | 3 |
| 150-190 | 7 | 8 | 2 |
| 150-190 | 7 | 8 | 2 |
| 150-190 | 7 | 8 | 2 |
| 150-190 | 8 | 8 | 2 |
| 150-190 | 7 | 12 | 2 |
| 80-100 | 3.5-4.0 | 6 | 3 |

In Table 2 a preferred upper limit of the wall thickness is provided for the various scaffolds. In addition to, or separate from these examples there can be a reduction in width of a strut. A reduced width can be desirable for clinical reasons. A width reduction can be up to 25%, e.g., a width reduction from 200 microns to 150 microns, of between 100 to 150 microns. For these embodiments the same flexural rigidity (E×I where E is Young's modulus and I the cross-section moment of inertia in the bending plane) may be achieved, but with a lower cross-sectional inertia needed to achieve the same radial strength for the scaffold.

Existing scaffolds have wall thicknesses from about 150 to 170 microns while metallic stents have thicknesses of 60 to 100 microns. It is desirable to have a scaffold profile as low as possible, more like a metal stent.

According to the disclosure, selected ranges of strut thickness for a scaffold having a 3 mm outer diameter include less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. More preferably a wall thickness of between 80 and 100 microns, and more preferably between 82 and 89 microns.

Selected ranges of strut thickness for a scaffold having 7, 8 or 9 mm outer diameters include less than 280 microns, less than 260 microns, less than 240 microns, about 190 micron, 149 to 186 microns, 149 to 220 microns, 170 to 190 microns, 170 to 210 microns, 210 to 220 microns. More preferably a wall thickness of between 150 and 190 microns for a scaffold having an outer diameter of 7, 8 or 9 mm.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method for making a medical device, comprising:
   forming a tube comprising a polymer or a polymer combination having a glass transition temperature (Tg);
   radially expanding the tube to increase polymer chain orientation in a circumferential direction, thereby increasing a radial strength of the tube, wherein the increased polymer chain orientation in the circumferential direction occurs to a greater degree nearer to an inner surface of the tube than an outer surface of the tube;

die drawing the radially expanded tube to increase polymer chain orientation in the circumferential direction to a greater degree nearer to the outer surface of the tube than the inner surface of the tube such that the polymer chain orientation from the inner surface to the outer surface of the die drawn tube is more uniform than that of the radially expanded tube; and making a scaffold from the die drawn tube.

2. The method of claim 1, wherein the tube is substantially or completely a blend of polylactide (PLA) and a PLA and polycaprolactone (PCL) random copolymer (20% PCL) and the blended PLA-PCL combination has between about 1% to 5% by weight PCL.

3. The method of claim 1, wherein prior to radial expansion the tube is an amorphous tube.

4. The method of claim 1, wherein the tube is radially expanded by blow molding, wherein the ratio of RE/AE is between about 2 to 1, 2.5 to 1, 3 to 1, or 4 to 1.

5. The method of claim 1, wherein the die drawing includes pulling the radially expanded tube through a die that reduces or increases a diameter of the tube.

6. The method of claim 1, wherein the die drawing includes pulling the tube through a die that is devoid of a mandrel.

7. The method of claim 1, wherein the die drawing includes pulling the radially expanded tube through a die that includes a flat or tapered mandrel.

8. The method of claim 1, wherein an inner draw ratio of the die drawn tube is lower than an outer diameter draw ratio of the radially expanded tube.

9. The method of claim 8, wherein during the die drawing the scaffold has a temperature of about 10 to 20, 5-20 or 20-30° C. above Tg.

10. The method of claim 1, further including:

crimping the scaffold to a balloon, the balloon having an inflated diameter and the scaffold having a pre-crimp inner diameter before crimping and crimped diameter after crimping, wherein the scaffold undergoes a plastic deformation when crimped to the balloon, and wherein the scaffold pre-crimp inner diameter is greater than the balloon inflated diameter.

11. The method of claim 1, wherein processing parameters for the die drawing step include (a) a Die Temperature (Td) between about 10 and 35° C. above Tg;

(b) a Steady State Draw Speed (Vd) of between 0.1 mm/sec and 25 mm/sec;

(c) a Die Taper angle and/or mandrel angle between 15 and 60 degrees;

(d) a Pre-Heat Temperature (Tp) about 5-10° C. below Tg; and (e) a Temperature difference between a pre-heat chamber and a die (Delta-Tin) of about 10 to 40° C.

12. The method of claim 11, wherein the die drawing step is performed using a die having an exit, the method further including a quenching step after the die drawing step, wherein processing parameters for the quenching step include (a) the tube temperature drops below 5-10Deg. C. less than Tg within 1-2 sec of a die drawn tube portion passing through the exit, (b) a cooling chamber disposed adjacent the exit has a cooling chamber temperature between about 5-10Deg. C. and cools the drawn tube portion to about 15° C. when the tube portion is about 25 mm from the exit; and (c) a temperature difference between the die and the cooling chamber is about 50 to 80° C.

13. The method of claim 1, wherein a tube outer diameter for the radially expanded tube is between about 0.6 and 0.2 inches and a wall thickness is between about 0.02 and 0.01 inches.

14. The method of claim 1, wherein the tube is radially expanded by blow molding to produce a blow-molded tube, wherein a hardness at an inner surface of the blow-molded tube is substantially different from a hardness at an outer surface of the blow-molded tube, and wherein a hardness of the die drawn tube is about the same at an inner and outer surface of the die drawn tube.

15. The method of claim 1, wherein the radially expanding of the tube applies a first radial expansion to the tube to produce the radially expanded tube, wherein the first radial expansion has a first radial draw of R1, the die drawing applies a second radial expansion and/or contraction to the radially-expanded tube to produce a second radial draw of R2, and wherein an axial draw associated with R2 is substantially greater than an axial draw associated with R1.

16. The method of claim 1, wherein a hardness at the inner surface of the die-drawn tube is about the same as the hardness at the outer surface.

17. The method of claim 1, wherein the polymer chain orientation in an axial direction of orientation from the inner surface to the outer surface of the die drawn tube is not uniform.

* * * * *